(12) United States Patent
Yun

(10) Patent No.: US 12,702,852 B2
(45) Date of Patent: Aug. 11, 2026

(54) APPARATUS FOR TREATING URINARY INCONTINENCE USING MAGNETIC FIELD

(71) Applicant: DAEYANG MEDICAL CO., LTD., Wonju-si (KR)

(72) Inventor: Jeong-Sub Yun, Wonju-si (KR)

(73) Assignee: DAEYANG MEDICAL CO., LTD., Wonju-si (KR)

( * ) Notice: Subject to any disclaimer, the term of this patent is extended or adjusted under 35 U.S.C. 154(b) by 861 days.

(21) Appl. No.: 18/017,290

(22) PCT Filed: Jul. 23, 2021

(86) PCT No.: PCT/KR2021/009526
§ 371 (c)(1),
(2) Date: Jan. 20, 2023

(87) PCT Pub. No.: WO2022/019695
PCT Pub. Date: Jan. 27, 2022

(65) Prior Publication Data

US 2023/0293901 A1 Sep. 21, 2023

(30) Foreign Application Priority Data

Jul. 23, 2020 (KR) ........................ 10-2020-0091341
Jul. 22, 2021 (KR) ........................ 10-2021-0096120

(51) Int. Cl.
*A61N 2/00* (2006.01)

(52) U.S. Cl.
CPC .................................... *A61N 2/004* (2013.01)

(58) Field of Classification Search
CPC ........... A61N 2/004; A61N 2/006; A61N 2/02
See application file for complete search history.

(56) References Cited

U.S. PATENT DOCUMENTS 5,984,854 A * 11/1999 Ishikawa .................. A61N 2/02 600/9
6,179,769 B1 1/2001 Ishikawa et al.
(Continued)

FOREIGN PATENT DOCUMENTS

KR 10-2004-0052957 A 6/2004
KR 10-2010-0130011 A 12/2010
(Continued)

OTHER PUBLICATIONS

International Search Report dated Nov. 9, 2021, issued in counterpart International Application No. PCT/KR2021/009526 (3 pages).

*Primary Examiner* — Alex M Valvis
*Assistant Examiner* — Lara Linh Tran
(74) *Attorney, Agent, or Firm* — WHDA, LLP

(57) ABSTRACT

Proposed is an apparatus for treating urinary incontinence using a magnetic field. The apparatus includes: a plurality of magnetic field generation units that apply magnetic fields to different muscles of a patient, the muscles being muscles that affect the treatment of the urinary incontinence of the patient; a control unit for controlling the operation of the plurality of magnetic field generation units; and a power supply unit for supplying power to the magnetic field generation units and the control unit. The apparatus simultaneously stimulates the major muscles that affect urinary incontinence, thereby improving the effect of treating urinary incontinence.

14 Claims, 9 Drawing Sheets

(56) References Cited

U.S. PATENT DOCUMENTS

| | | | | |
|---|---|---|---|---|
| 6,223,750 | B1 * | 5/2001 | Ishikawa | A61N 2/006 128/885 |
| 7,338,417 | B2 * | 3/2008 | Kang | A61B 5/224 482/148 |
| 10,363,846 | B2 * | 7/2019 | Gallagher | A61N 2/02 |
| 2006/0187607 | A1 * | 8/2006 | Mo | A61N 2/02 361/143 |

FOREIGN PATENT DOCUMENTS

| | | | |
|---|---|---|---|
| KR | 10-1772687 | B1 | 8/2017 |
| KR | 10-1901215 | B1 | 9/2018 |

* cited by examiner

FIG. 1

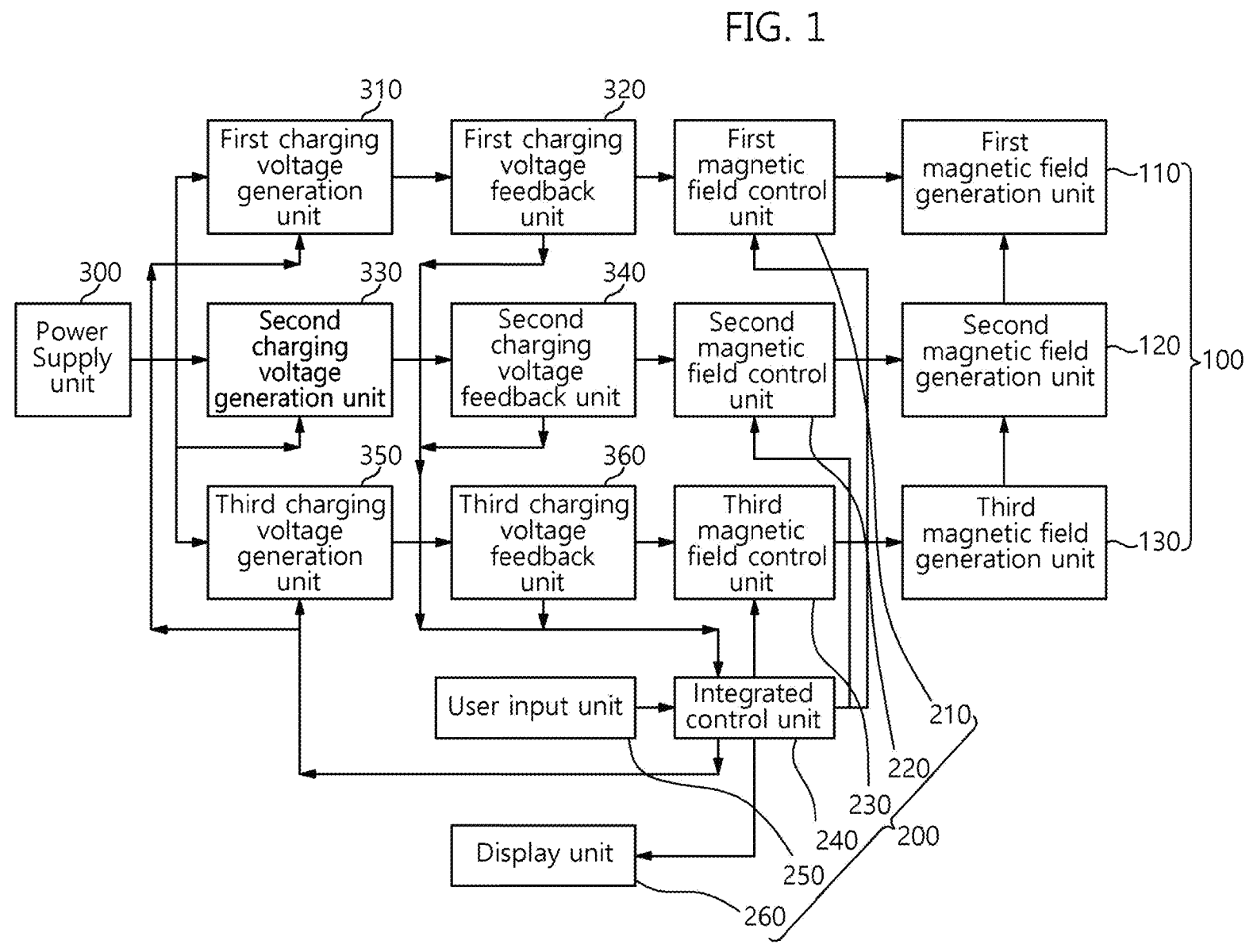

100
110 First magnetic field generation unit
120 Second magnetic field generation unit
130 Third magnetic field generation unit
200
210 First magnetic field control unit
220 Second magnetic field control unit
230 Third magnetic field control unit
240 Integrated control unit
250 User input unit
260 Display unit
300 Power Supply unit
310 First charging voltage generation unit
320 First charging voltage feedback unit
330 Second charging voltage generation unit
340 Second charging voltage feedback unit
350 Third charging voltage generation unit
360 Third charging voltage feedback unit freq
time
intensity
time freq
time
intensity
time freq
time
intensity
time freq
time
intensity
time freq
time
intensity
time

APPARATUS FOR TREATING URINARY INCONTINENCE USING MAGNETIC FIELD

TECHNICAL FIELD

The present disclosure relates to an apparatus for treating urinary incontinence using a magnetic field. The apparatus is to treat urinary incontinence by stimulating the adductor muscles or transversus abdominis muscle, in addition to the pelvic floor muscles, with magnetic fields.

BACKGROUND ART

In general, urinary incontinence is an unintentional, involuntary leakage of urine, and is a condition of abnormal urination that creates social or hygienic problems.

The main treatment for urinary incontinence has been surgery. In recent years, however, non-surgical treatments are preferred due to possible complications associated with surgery, and only a small number of patients with severe symptoms undergo surgery.

Non-surgical treatment options for urinary incontinence include pelvic floor muscle exercises (Kegels), biofeedback, electrical stimulation therapy, and magnetic field stimulation therapy.

Kegels exercises is the most basic and traditional method and an economical and effective way of treatment, but it is difficult for patients to correctly perform Kegels exercises, which leads to unsatisfactory treatment results.

Biofeedback helps to exercise the pelvic floor muscles correctly and can be used as an adjunct to pelvic floor muscle exercises, but has the inconvenience of having to take off clothes and insert a probe into the vagina.

Electrical stimulation can be used to assist in strengthening pelvic floor muscles by involuntarily (passively) contracting pelvic muscles through a transmission of electrical impulses, but this technique also has the inconvenience of having to take off clothes and insert a probe into the vagina.

Magnetic field stimulation is based on the same principle as the electrical stimulation, involves electric currents that work more effectively on motor nerves than on sensory nerves, and can be used to supplement the electrical stimulation. In addition, the magnetic field stimulation is an effective non-surgical method and the most non-invasive treatment for urinary incontinence.

However, in the case of conventional magnetic field stimulation, usually one magnetic field probe is provided and only the pelvic floor muscles are stimulated with a magnetic field, which leads to unsatisfactory treatment results.

DISCLOSURE

Technical Problem

The present disclosure has been made keeping in mind the problems occurring in the related art. An objective of the present disclosure is to provide an apparatus for treating urinary incontinence using a magnetic field, which improves effect of treating urinary incontinence by stimulating major muscles involved in urinary incontinence using a plurality of magnetic field probes.

An objective of the present disclosure is to provide an apparatus for treating urinary incontinence using a magnetic field, which further improves effect of treating urinary incontinence by applying stimulation in a complex manner from magnetic field probes and maximizes effect of treating urinary incontinence in a short time.

An objective of the present disclosure is to provide an apparatus for treating urinary incontinence using a magnetic field, which further improves an effect of treating urinary incontinence by adjusting the position of each magnetic field probe that applies a magnetic field to major muscles involved in urinary incontinence according to the patient's muscle condition or posture.

Technical Solution

In order to achieve the above mentioned objective, according to an embodiment of the present disclosure, there is provided an apparatus for treating urinary incontinence using a magnetic field. The apparatus includes: magnetic field generation units configured to apply magnetic fields to different muscles of a patient, the muscles being muscles that affect a treatment of the urinary incontinence of the patient; a control unit configured to control an operation of the magnetic field generation units; and a power supply unit configured to supply power to the magnetic field generation units and the control unit.

In the present disclosure, the magnetic field generation units may include: a first magnetic field generation unit configured to apply a magnetic field to pelvic floor muscles of the patient; and a second magnetic field generation unit configured to apply a magnetic field to adductor muscles of the patient.

In the present disclosure, the magnetic field generation units may further include: a third magnetic field generation unit configured to apply a magnetic field to a transversus abdominis muscle of the patient.

In the present disclosure, the control unit may include a treatment mode unit for treating urinary incontinence according to a predetermined stimulation area and stimulation sequence, and a user mode unit with which a patient or an operator is able to select a stimulation area and stimulation sequence, wherein the treatment mode unit may include a predetermined stimulation area, and treatment modes for stimulating the predetermined stimulation area according to a predetermined sequence, wherein the treatment modes may include: a circulation operation mode in which the first magnetic field generation unit, the second magnetic field generation unit, and the third magnetic field generation unit are operated cyclically in random order but operated individually; a complex stimulation cycle mode in which at least two of the first magnetic field generation unit, the second magnetic field generation unit, and the third magnetic field generation unit are operated at the same time to apply complex stimulation, but different complex stimulations are applied cyclically; and a sequential stimulation treatment mode in which the first magnetic field generation unit, the second magnetic field generation unit, and the third magnetic field generation unit are operated sequentially in random order.

In the present disclosure, the control unit may control operations of the first magnetic field generation unit, the second magnetic field generation unit, and the third magnetic field generation unit to generate magnetic fields having at least two different stimulation patterns.

The embodiment of an apparatus for treating urinary incontinence using a magnetic field according to the present disclosure may further include: a seat portion on which the first magnetic field generation unit and the second magnetic field generation unit are located and on which a patient sits.

The embodiment of an apparatus for treating urinary incontinence using a magnetic field according to the present disclosure may further include: a seat portion on which the first magnetic field generation unit and the second magnetic field generation unit are located and on which a patient sits; and a backrest portion that is built on a rear side of the seat portion to support the patient's back and on which the third magnetic field generation unit is located.

The embodiment of an apparatus for treating urinary incontinence using a magnetic field according to the present disclosure may further include: a first arm member and a second arm member rotatably connected to each side of the backrest portion; a first transverse abdominis cover plate member connected to an end of the first arm member, equipped with the third magnetic field generation unit, and positioned to cover the transversus abdominis muscle connected to a side of an abdomen; and a second transverse abdominis cover plate member connected to an end of the second arm member, equipped with the third magnetic field generation unit, and positioned to cover the transversus abdominis muscle connected to a side of the abdomen.

The embodiment of an apparatus for treating urinary incontinence using a magnetic field according to the present disclosure may further include: a spacing adjustment moving unit configured to adjust a distance between the first transverse abdominis cover plate member and the second transverse abdominis cover plate member by moving the first transverse abdominis cover plate member and the second transverse abdominis cover plate member in a width direction of the backrest portion.

In the present disclosure, on each side of the backrest portion, a first connection arm member to which the first arm member is rotatably connected, and a second connection arm member to which the second arm member is rotatably connected may be respectively positioned, and wherein the spacing adjustment moving unit may include: moving screw units screwed into the first connection arm member and the second connection arm member, but in opposite directions to each other, to be rotatably positioned; and a rotary motor configured to rotate the moving screw unit.

The embodiment of an apparatus for treating urinary incontinence using a magnetic field according to the present disclosure may further include: a first probe moving unit located on the seat portion and configured to move a first magnetic field probe of the first magnetic field generation unit; and a second probe moving unit configured to move a second magnetic field probe of the second magnetic field generation unit.

In the present disclosure, the first probe moving unit may include: an X-axis linear moving portion for a first probe on which the first magnetic field probe is mounted, and configured to linearly reciprocate the mounted first magnetic field probe in an X-axis direction; and a Y-axis linear moving portion for a first probe configured to linearly move the X-axis linear moving portion for a first probe in a Y-axis direction, and the second probe moving unit may include: an X-axis linear moving portion for a second probe on which the second magnetic field probe is mounted, and configured to linearly reciprocate the mounted second magnetic field probe in the X-axis direction; and a Y-axis linear moving portion for a second probe configured to linearly move the X-axis linear moving portion for a second probe in the Y-axis direction.

The embodiment of an apparatus for treating urinary incontinence using a magnetic field according to the present disclosure may further include: seat pressure sensors provided to be spaced apart on the seat portion and detect pressure generated when the patient sits down, wherein the control unit may receive pressure values from the seat pressure sensors, check the body shape and posture of the seated patient, and, according to the body shape and posture of the patient, position the first magnetic field probe and the second magnetic field probe to face the pelvic floor muscles and the adductor muscles, respectively, for treatment of urinary incontinence by means of the first probe moving unit and the second probe moving unit.

The embodiment of an apparatus for treating urinary incontinence using a magnetic field according to the present disclosure may further include: a first probe moving unit located on the seat portion and configured to move a first magnetic field probe of the first magnetic field generation unit; a second probe moving unit configured to move a second magnetic field probe of the second magnetic field generation unit; and a third probe moving unit configured to move a third magnetic field probe of the third magnetic field generation unit.

In the present disclosure, the first probe moving unit may include: an X-axis linear moving portion for a first probe on which the first magnetic field probe is mounted, and configured to linearly reciprocate the mounted first magnetic field probe in an X-axis direction; and a Y-axis linear moving portion for a first probe configured to linearly move the X-axis linear moving portion for a first probe in a Y-axis direction, the second probe moving unit may include: an X-axis linear moving portion for a second probe on which the second magnetic field probe is mounted, and configured to linearly reciprocate the mounted second magnetic field probe in the X-axis direction; and a Y-axis linear moving portion for a second probe configured to linearly move the X-axis linear moving portion for a second probe in the Y-axis direction, and the third probe moving unit may include: an X-axis linear moving portion for a third probe on which the third magnetic field probe is mounted, and configured to linearly reciprocate the mounted third magnetic field probe in the X-axis direction; and a Y-axis linear moving portion for a third probe configured to linearly move the X-axis linear moving portion for a third probe in the Y-axis direction.

The embodiment of an apparatus for treating urinary incontinence using a magnetic field according to the present disclosure may further include: seat pressure sensors provided to be spaced apart on the seat portion and detect pressure generated when the patient sits down; and backrest pressure sensors provided to be spaced apart on the backrest portion and detect pressure generated when the patient leans against the backrest portion, wherein the control unit may receive pressure values from the seat pressure sensors and the backrest pressure sensors, check the body shape and posture of the seated patient, and, according to the body shape and posture of the patient, position the first magnetic field probe, the second magnetic field probe, and the third magnetic field probe to face the pelvic floor muscles, the adductor muscles, and the transversus abdominis muscle, respectively, for treatment of urinary incontinence by means of the first probe moving unit, the second probe moving unit, and the third probe moving unit.

In the present disclosure, the seat portion may include a seat casing portion where the first magnetic field generation unit and the second magnetic field generation unit are located, wherein the seat casing portion may include: a seat body casing member having an open upper surface; a seat casing cover member configured to cover the open upper surface of the seat body casing member, and a seat cover elastic support configured to elastically support the seat casing cover member, wherein the seat cover elastic support may include: seat cover moving members protruding toward a lower side of the seat casing cover member and movably inserted into a side surface of the seat body casing member, and a seat cover spring member located in a side portion of the seat body casing member and elastically supporting the seat cover moving members, wherein at an upper end of the seat cover moving members, a ball joint rotatably coupled to the seat casing cover member may be located.

In the present disclosure, the backrest portion may include a backrest casing portion where the third magnetic field generation unit is located, wherein the backrest casing portion may include: a backrest body casing member having an open upper surface; a backrest casing cover member configured to cover the open upper surface of the backrest body casing member, and a backrest cover elastic support configured to elastically support the backrest casing cover member, wherein the backrest cover elastic support may include: backrest cover moving members protruding toward a rear side of the backrest casing cover member and movably inserted into a side surface of the backrest body casing member; and a backrest cover spring member located in a side surface of the backrest body casing member and elastically supporting the backrest cover moving members, wherein at one end of the backrest cover moving members, a ball joint rotatably coupled to the backrest casing cover member may be located.

Advantageous Effects

The present disclosure can improve effect of treating urinary incontinence by simultaneously stimulating major muscles involved in urinary incontinence using a plurality of magnetic field probes.

The present disclosure can further improve effect of treating urinary incontinence by mixing frequencies generated and forms of stimulation applied by a plurality of magnetic field probes or by using interference waves generated by the probes that generate different frequencies.

The present disclosure can further improve effect of treating urinary incontinence by adjusting the position of each magnetic field probe that applies magnetic field stimulation to muscles according to the patient's muscle condition or posture.

DESCRIPTION OF DRAWINGS

FIG. 1 is a block diagram showing an embodiment of an apparatus for treating urinary incontinence using a magnetic field according to the present disclosure;

FIG. 3 is a perspective view showing the embodiment of an apparatus for treating urinary incontinence using a magnetic field according to the present disclosure;

FIGS. 5 and 6 are views showing examples of a probe moving unit in the embodiment of an apparatus for treating urinary incontinence using a magnetic field according to the present disclosure;

DESCRIPTION OF NUMERALS

Figures 2A, 2B, 2C, 2D, 2E:
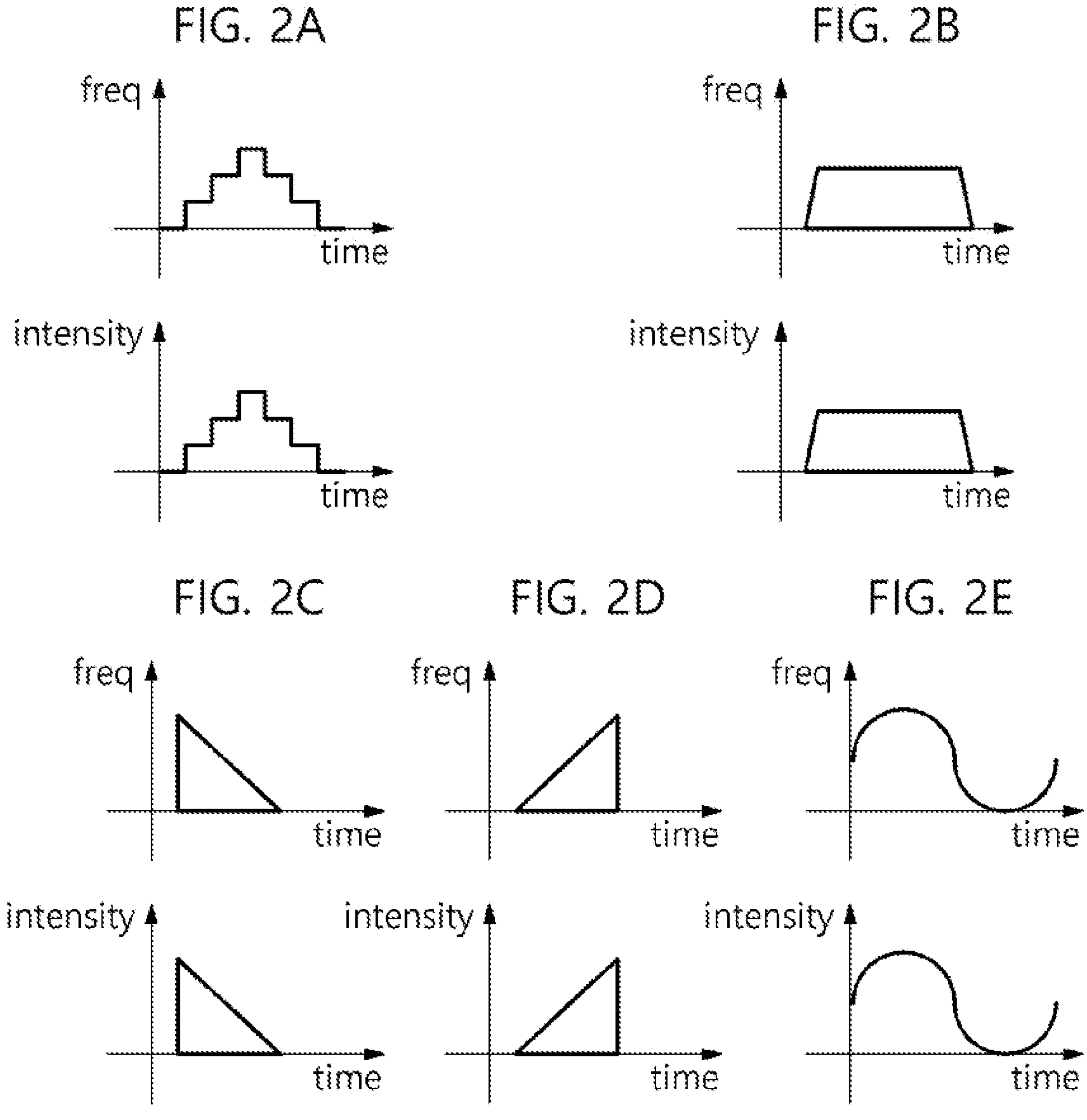
FIGS. 2A to 2E are views showing stimulation patterns in the embodiment of an apparatus for treating urinary incontinence using a magnetic field according to the present disclosure.

100: magnetic field generation unit 110: first magnetic field generation unit
120: second magnetic field generation unit 130: third magnetic field generation unit
200: control unit 210: first magnetic field control unit
220: second magnetic field control unit 230: third magnetic field control unit
240: integrated control unit 250: user input unit
260: display unit 300: power supply unit
310: first charging voltage generation unit 320: first charging voltage feedback unit
330: second charging voltage generation unit 340: second charging voltage feedback unit
350: third charging voltage generation unit 360: third charging voltage feedback unit
400: seat portion 400*a*: seat pressure sensor
400*b*: first pressure sensor portion 400*c*: second pressure sensor portion
401: seat support portion 402: footrest portion
410: seat body casing member 420: seat casing cover member
430: seat cover elastic support 431: seat cover moving member
432: seat cover spring member 500: backrest portion
500*a*: backrest pressure sensor 501: first arm member
502: second arm member 503: first transverse abdominis cover plate member
504: second transverse abdominis cover plate member 505: first connection arm member
506: second connection arm member 507: spacing adjustment moving unit
508: moving screw unit 508*a*: first screw
508*b*: second screw 509: rotary motor
510: power transmission unit 511: first bevel gear
512: second bevel gear 513: third bevel gear
520: backrest body casing member 530: backrest casing cover member
540: backrest cover elastic support 541: backrest cover moving member
542: backrest cover spring member 600: first probe moving unit
610: X-axis linear moving portion for a first probe 620: Y-axis linear moving portion for a first probe
700: second probe moving unit 710: X-axis linear moving portion for a second probe
720: Y-axis linear moving portion for a second probe 800: third probe moving unit
810: X-axis linear moving portion for a third probe 820: Y-axis linear moving portion for a third probe

BEST MODE

Hereinafter, the present disclosure will be described in more detail.

Preferred embodiments of the present disclosure will be described in detail with reference to the accompanying drawings. Prior to the detailed description of the present disclosure, the terms or words used in this specification and claims described below should not be construed as being limited to common or dictionary meanings. The embodiments described in this specification and the configurations shown in the drawings are merely the most preferred embodiments of the present disclosure and do not represent all the technical ideas of the present disclosure. Therefore, it should be understood that there may be various equivalents and modifications that may be substituted for the embodiments and configurations at the time of this application.

The embodiments described in this specification and the configurations shown in the drawings are merely the most preferred embodiments of the present disclosure and do not represent all the technical ideas of the present disclosure. Therefore, it should be understood that there may be various equivalents and modifications that may be substituted for the embodiments and configurations at the time of this application.

FIG. 1 is a schematic diagram showing an embodiment of an apparatus for treating urinary incontinence using a magnetic field according to the present disclosure. Referring to FIG. 1, the embodiment of an apparatus for treating urinary incontinence using a magnetic field according to the present disclosure will be described in detail below.

Referring to FIG. 1, the embodiment of an apparatus for treating urinary incontinence using a magnetic field according to the present disclosure includes a plurality of magnetic field generation units 100 that individually apply magnetic fields to different muscles that affect urinary incontinence.

The magnetic field generation units 100 are positioned to apply magnetic fields to different muscles that affect the treatment of urinary incontinence of a patient.

For example, the magnetic field generation units 100 include: a first magnetic field generation unit 110 that applies a magnetic field to the patient's pelvic floor muscles; and a second magnetic field generation unit 120 that applies a magnetic field to the patient's adductor muscles.

The magnetic field generation units 100 may further include a third magnetic field generation unit 130 that applies a magnetic field to the transversus abdominis.

The pelvic floor is composed of muscle fibers of the levator ani, the coccygeus muscle, and associated connective tissue which span the bottom of the pelvis.

The adductors are a group of muscles which exist in the inner thigh, and the transversus abdominis is a broad muscle that runs across the abdomen, forming the third layer on either side of the abdomen.

That is, as an example, the first muscle that affects the treatment of urinary incontinence of a patient is pelvic floor muscles, the second muscle that affects the patient's urinary incontinence treatment is the adductors, and the third muscle that affects the patient's urinary incontinence treatment is the transversus abdominis.

In short, the muscles that affect urinary incontinence include the pelvic floor muscles (PFM), adductors, and transversus abdominis.

The pelvic floor muscles are one of these core muscles, located at the bottom of the pelvis. The etymology of pelvis is a washbasin, and the pelvis is like a washbasin that holds the intestines. Here, the bottom of the washbasin corresponds to the pelvic floor muscles.

Because of these pelvic floor muscles, the organs do not go down due to gravity.

The pelvic floor muscles are the muscles that work when urinating and have the most direct effect on urinary incontinence.

The pelvic floor muscles are the muscles at the bottom of the two iliac bones and the sacrum, with the vagina in front and the anus behind.

The pelvic floor consists of the endopelvic, pelvic diaphragm, and urogenital diaphragm (Sejong Choi, 2009).

Among these three, the endopelvic is a meshwork of smooth muscle fibers, ligaments, nerves, blood vessels, and soft tissues entangled around the urethral meatus, ischiocavernosus muscle, vaginal opening, ischial tuberosity, anal sphincter, coccyx, so voluntary movement is impossible and thus muscle-strengthening exercises cannot be performed. The pelvic diaphragm is a muscular layer in the lower urethral triangle that serves to support the pelvic organs and is innervated by the pudendal nerve and rapidly contracts to maintain urinary containment during coughing and sneezing.

The urogenital diaphragm forms sphincter urethra loops around the urethra to enable micturition control, and can be voluntarily controlled to strengthen muscle through exercises (Se-jong Choi, 2009).

The adductor muscles exist in the inner thigh and consists of the adductor brevis, adductor longus, and adductor magnus, which are responsible for adduction of the femur and hip joint. [FIG. 2] As shown in the anatomical shape of the adductors, all three adductor muscles anatomically originate from the pelvis, such as the pubic bone, and are connected to the inner or posterior part of the femur. According to the research results published in the Journal of the Korean Society for Exercise Rehabilitation by Yoon Jae-Ryang, Lee Mi-Suk, Lee Mun-Jin, etc. (2010), the anatomical location of the adductor muscles means that it is correlated with the contractile force of the pelvic floor muscles such as the sphincter.

According to the results of a 4-week "adductor" exercise conducted by Seong-hoon Na, Gil-young Cheon, Yong-bal Yun, Cheol-won Lee, etc. (2010) targeting middle-aged women, lower extremity adductor strengthening exercise for middle-aged women can influence vaginal contraction pressure and relieve urinary incontinence symptoms.

In addition, according to the research results presented by Peschers, U. M., Gingelmaier, A., Jundt, K., Leib, B., Dimpfl, T., etc. (2001), women use their adductors to contract their pelvic floor muscles. Considering the results of many previous studies such as the above, the adductors are muscles that have a very close effect on urinary incontinence. Thus, it is necessary to strengthen the adductor muscles to relieve the symptoms of urinary incontinence.

The transverse abdominis muscle is the deepest of the abdominal muscles, cannot be touched, and is the only abdominal muscle with fibers that are arranged in parallel (arranged in a horizontal direction) (Jin-woo Jeong, 2014). The transverse abdominis surrounds organs such as the stomach, small intestine, and large intestine, etc., and the adductor group including the adductor brevis muscle, adductor lingus muscle, and adductor magnus muscle like a corset. The transverse abdominis determines the size of the space within the abdomen and plays a role in maintaining the stability of the lumbar spine and body balance (Hodges, P. W. & Gandervia, S. C., 2000). Although the primary function of the transversus abdominis is to rotate the trunk, the transversus abdominis provides segmental stability of the spine by increasing internal abdominal pressure. In addition, the transversus abdominis plays a role in controlling precise movement of the trunk so that only necessary movement can occur. The transversus abdominis is the first muscle that contracts deep inside when a person moves his/her arms and legs.

A number of previous studies have reported that the function of the transversus abdominis is related to the pelvic floor muscles and consequently affects urinary incontinence. Isacowitz, R. (2006) claimed that the muscles of the body were intricately intertwined, so when the transverse abdominis contracted, the pelvic floor muscles also contracted. Sapsford, R. R., Hodges, P. W., Richardson, C. A., Cooprer, D. H., Markwell, S. J., Jull, G. A. (2001), etc. presented research results that when the pelvic floor muscles were contracted, the transverse abdominis muscles were activated the most regardless of the posture of the lumbar spine, and conversely, as a result of various isometric contraction tests for the abdominal muscles, electromyographic (EMG) activation of the pubis coccyx and external anal sphincter increased.

Neumann, P., Gill, V. (2002) suggested an indirect muscle strengthening exercise method that simultaneously contracts both muscles by examining the activity of the pelvic floor muscles and abdominal muscles with EMG. Dumoulin, C., Lemieux, M. C., Bourbonnais, D., Gravel, D., Bravo, C., Morin, M. (2004) studied the effect of a pelvic floor muscle exercise method that includes abdominal muscle exercise at the same time. Hung, H. C., Hslao, S. M. Chif, S. Y., Lin, H. H., Tsauo, J. Y. (2010) proposed a method of training the combined function of the diaphragm, deep muscles, and pelvic floor muscles as a way to relieve symptoms of urinary incontinence. Bo, K., Morkved, S., Frawley, H., Sherbum, M. (2009) reported that a muscle strengthening method using pelvic floor muscles and transversus abdominis was effective in treating urinary incontinence.

In short, the results of many studies confirm that the pelvic floor muscles, adductors, and transversus abdominis are the main muscles involved in the treatment of urinary incontinence.

In the present disclosure, as an example, the first magnetic field generation unit 110 is positioned to apply a magnetic field to the pelvic floor muscles of a patient, the second magnetic field generation unit 120 is positioned to apply a magnetic field to the adductor muscles of the patient, and the third magnetic field generation unit 130 is positioned to generate a magnetic field in the patient's transverse abdominis muscle.

The first magnetic field generation unit 110, the second magnetic field generation unit 120, and the third magnetic field generation unit 130, that is, each of the plurality of magnetic field generation units 100 includes an electrode, that is, a magnetic field probe that applies a magnetic field. The magnetic field probe generates a magnetic field having a frequency value within a preset frequency range through a current flowing by power supplied from a power supply unit 300.

As an example, the magnetic field probe is formed in the form of a coil and current flows to generate a pulsed magnetic field having a frequency value. In addition, the magnetic field probe may be variously modified and implemented with a known structure capable of generating a pulse magnetic field, so a detailed description is omitted.

The operation of the plurality of magnetic field generation units 100, that is, the first magnetic field generation unit 110, the second magnetic field generation unit 120, and the third magnetic field generation unit 130 is controlled by a control unit 200.

The control unit 200 and the plurality of magnetic field generation units 100 may be operated by receiving power from the power supply unit 300.

The first magnetic field generation unit 110, the second magnetic field generation unit 120, and the third magnetic field generation unit 130 are operated by individually receiving power from the power supply unit 300. The operation of the first magnetic field generation unit 110, the second magnetic field generation unit 120, and the third magnetic field generation unit 130 is controlled by the control unit 200 to individually generate pulsed magnetic fields.

The embodiment of an apparatus for treating urinary incontinence using a magnetic field according to the present disclosure further includes: a plurality of charging voltage generation units for generating charging voltages supplied to the plurality of magnetic field generation units 100 and the control unit 200; and a plurality of charging voltage feedback units for feeding back the charging voltages supplied to the plurality of magnetic field generation units 100 and the control unit 200.

In addition, the control unit 200 includes: a first magnetic field control unit 210 for controlling the operation of the first magnetic field generation unit 110; a second magnetic field control unit 220 for controlling the operation of the second magnetic field generation unit 120; a third magnetic field control unit 230 for controlling the operation of the third magnetic field generation unit 130; an integrated control unit 240 for controlling the operation of the first magnetic field control unit 210, the second magnetic field control unit 220, and the third magnetic field control unit 230; a user input unit 250 through which a patient may enter and select treatment information; and a display unit 260 that outputs control information.

That is, the control unit 200 is provided with the magnetic field control units 210, 220, and 230 for individually controlling the magnetic field generation units 100, and includes: the integrated control unit 240 that integrates and controls the magnetic field control units 210, 220, and 230; the user input unit 250 through which a patient may enter and select treatment information; and the display unit 260 that outputs control information.

To be specific, the embodiment of an apparatus for treating urinary incontinence using a magnetic field according to the present disclosure further includes: a first charging voltage generation unit 310 that generates a charging voltage for supplying power from the power supply unit 300 to the first magnetic field generation unit 110 and the control unit 200; a first charging voltage feedback unit 320 that feeds back the charging voltage supplied to the first magnetic field generation unit 110 and the control unit 200; a second charging voltage generation unit 330 that generates a charging voltage for supplying power from the power supply unit 300 to the second magnetic field generation unit 120 and the control unit 200; a second charging voltage feedback unit 340 that feeds back the charging voltage supplied to the second magnetic field generation unit 120 and the control unit 200; a third charging voltage generation unit 350 that generates a charging voltage for supplying power from the power supply unit 300 to the third magnetic field generation unit 130 and the control unit 200; and a third charging voltage feedback unit 360 that feeds back the charging voltage supplied to the third magnetic field generation unit 130 and the control unit 200.

The first magnetic field generation unit 110 and the first magnetic field control unit 210 are operated by receiving power through the first charging voltage generation unit 310 and the first charging voltage feedback unit 320, and the operation of the first magnetic field generation unit 110 may be controlled by the first magnetic field control unit 210.

In addition, the second magnetic field generation unit 120 and the second magnetic field control unit 220 are operated by receiving power through the second charging voltage generation unit 330 and the second charging voltage feedback unit 340, and the operation of the second magnetic field generation unit 120 may be controlled by the second magnetic field control unit 220.

In addition, the third magnetic field generation unit 130 and the third magnetic field control unit 230 are operated by receiving power through the third charging voltage generation unit 350 and the third charging voltage feedback unit 360, and the operation of the third magnetic field generation unit 130 may be controlled by the third magnetic field control unit 230.

Meanwhile, the control unit 200 includes: a treatment mode unit for treating urinary incontinence according to a predetermined stimulation area and stimulation sequence; and a user mode unit with which a patient may select the stimulation area and stimulation sequence, and may select and operate the treatment mode unit and the user mode unit through the user input unit 250.

The treatment mode unit includes a predetermined stimulation area and a plurality of treatment modes for stimulating the predetermined stimulation area in a predetermined sequence, and the patient may select one of the plurality of treatment modes.

The treatment modes may include a circulation operation mode in which the first magnetic field generation unit 110, the second magnetic field generation unit 120, and the third magnetic field generation unit 130 are operated cyclically in random order but operated individually.

To be specific, the treatment mode may include a first circulation operation mode in which the first magnetic field generation unit 110, the second magnetic field generation unit 120, and the third magnetic field generation unit 130 are sequentially operated in a circular manner.

In the first circulation operation mode, the following process is repeated. The first magnetic field generation unit 110 stops after operating for a predetermined time, and after the first magnetic field generation unit 110 is stopped, the second magnetic field generation unit 120 operates for a predetermined time and then stops, and after the second magnetic field generation unit 120 is stopped, the third magnetic field generation unit 130 operates for a predetermined time and then stops.

That is, in the first circulation operation mode, the first magnetic field generation unit 110, the second magnetic field generation unit 120, and the third magnetic field generation unit 130 are sequentially operated, but after the operation of the third magnetic field generation unit 130, the first magnetic field generation unit 110 to the third magnetic field generation unit 130 are again sequentially operated in turn so that the first magnetic field generation unit 110, the second magnetic field generation unit 120, and the third magnetic field generation unit 130 sequentially operated in a circular manner, thereby sequentially and cyclically stimulating the pelvic floor muscles, adductor muscles, and transversus abdominis muscle.

In addition, the treatment mode may include a second circulation operation mode in which the second magnetic field generation unit 120, the first magnetic field generation unit 110, and the third magnetic field generation unit 130 are sequentially operated in a circular manner.

In the second circulation operation mode, the following process is repeated. The second magnetic field generation unit 120 stops after operating for a predetermined time, and after the second magnetic field generation unit 120 is stopped, the first magnetic field generation unit 110 operates for a predetermined time and then stops, and after the first magnetic field generation unit 110 is stopped, the third magnetic field generation unit 130 operates for a predetermined time and then stops.

That is, in the second circulation operation mode, the second magnetic field generation unit 120, the first magnetic field generation unit 110, and the third magnetic field generation unit 130 are sequentially operated, but after the operation of the third magnetic field generation unit 130, the second magnetic field generation unit 120 to the third magnetic field generation unit 130 are again sequentially operated in turn so that the second magnetic field generation unit 120, the first magnetic field generation unit 110, and the third magnetic field generation unit 130 sequentially operated in a circular manner, thereby sequentially and cyclically stimulating the adductor muscles, pelvic floor muscles, and transversus abdominis muscle.

In addition, the treatment mode may include a complex stimulation cycle mode in which at least two of the first magnetic field generation unit 110, the second magnetic field generation unit 120, and the third magnetic field generation unit 130 are operated at the same time to apply complex stimulation, but different complex stimulations are applied cyclically.

To be specific, the treatment mode may include a first complex stimulation cycle mode in which the first magnetic field generation unit 110 and the second magnetic field generation unit 120 are simultaneously operated and then the first magnetic field generation unit 110 and the third magnetic field generation unit 130 are simultaneously operated, and this cycle is repeated.

In the first complex stimulation cycle mode, the following process is repeated. The first magnetic field generation unit 110 and the second magnetic field generation unit 120 operate for a predetermined time and stop, and then the first magnetic field generation unit 110 and the third magnetic field generation unit 130 operate for a predetermined time and stop.

In the first complex stimulation cycle mode, the first magnetic field generation unit 110 and the second magnetic field generation unit 120 are operated simultaneously to stimulate the pelvic floor muscles and adductor muscles at the same time, and then the first magnetic field generation unit 110 and the third magnetic field generation unit 130 are operated simultaneously to stimulate the pelvic floor muscles and transversus abdominis muscle at the same time, and this cycle is repeated.

In addition, the treatment mode may include a second complex stimulation cycle mode in which the second magnetic field generation unit 120 and the third magnetic field generation unit 130 operate simultaneously after the first magnetic field generation unit 110 operates, and this cycle is repeated.

In the second complex stimulation cycle mode, the following process is repeated. The first magnetic field generation unit 110 operates for a predetermined time and stops, and then the second magnetic field generation unit 120 and the third magnetic field generation unit 130 operate for a predetermined time and stop.

In the second complex stimulation cycle mode, the first magnetic field generation unit 110 is operated to stimulate the pelvic floor muscles, and then the second magnetic field generation unit 120 and the third magnetic field generation unit 130 are operated simultaneously to stimulate the adductor muscles and transversus abdominis muscle at the same time, and this cycle is repeated.

In addition, the treatment mode may further include a third complex stimulation cycle mode in which the first magnetic field generation unit 110, the second magnetic field generation unit 120, and the third magnetic field generation unit 130 operate simultaneously and stop in a circular manner.

In the third complex stimulation cycle mode, the cycle of simultaneously operating the first magnetic field generation unit 110, the second magnetic field generation unit 120, and the third magnetic field generation unit 130 for a predetermined time and stopping the operation is repeated so that simultaneous stimulation of the pelvic floor muscles, adductor muscles and transversus abdominis muscle for a predetermined time is repeated.

In the apparatus for treating urinary incontinence using a magnetic field according to the present disclosure, the pelvic floor muscles, adductors, and transversus abdominis muscle are individually stimulated in the circulation operation mode at the beginning of treatment so that a patient may get used to the stimulation for each treatment area at the beginning of treatment.

In addition, the complex stimulation cycle mode is selected after the patient becomes accustomed to the circulation operation mode to stimulate multiple muscles at the same time, thereby increasing treatment effects.

To be specific, at the beginning of treatment, the circulation operation mode is used to familiarize the patient with stimulation of the pelvic floor muscles, adductors, and transversus abdominis muscle. Next, in the middle of the treatment, the first complex stimulation cycle mode or the second complex stimulation cycle mode is used to familiarize the patient with complex stimulation of at least two of the pelvic floor muscles, adductors, and transversus abdominis muscle. Then, at the end of treatment, three muscles, namely the pelvic floor muscles, adductors, and transverse abdominis muscle are stimulated simultaneously for a predetermined time using the third complex stimulation cycle mode. As a result, the effectiveness of urinary incontinence treatment may be maximized.

Meanwhile, the treatment mode may further include a sequential stimulation treatment mode in which the first magnetic field generation unit 110, the second magnetic field generation unit 120, and the third magnetic field generation unit 130 are operated sequentially in random order.

The sequential stimulation treatment mode may include a first sequential stimulation treatment mode in which the operation is performed in the order of the second magnetic field generation unit 120, the first magnetic field generation unit 110, the third magnetic field generation unit 130, the first magnetic field generation unit 110, and the second magnetic field generation unit 120.

In the first sequential stimulation treatment mode, the second magnetic field generation unit 120 operates for a predetermined time and stops, and after the second magnetic field generation unit 120 is stopped, the first magnetic field generation unit 110 operates for a predetermined time and stops, and after the first magnetic field generation unit 110 is stopped, the third magnetic field generation unit 130 operates for a predetermined time and stops, and after the third magnetic field generation unit 130 is stopped, the first magnetic field generation unit 110 operates for a predetermined time and stops, and after the first magnetic field generation unit 110 is stopped, the second magnetic field generation unit 120 operates for a predetermined time and stops.

That is, in the first sequential stimulation treatment mode, the operation is performed in the order of the second magnetic field generation unit 120, the first magnetic field generation unit 110, the third magnetic field generation unit 130, the first magnetic field generation unit 110, and the second magnetic field generation unit 120 so that the adductors, pelvic floor muscles, transversus abdominis muscle, pelvic floor muscles, and adductors are stimulated sequentially in that order.

In addition, the sequential stimulation treatment mode may include a second sequential stimulation treatment mode in which the operation is performed in the order of the third magnetic field generation unit 130, the first magnetic field generation unit 110, the second magnetic field generation unit 120, the first magnetic field generation unit 110, and the third magnetic field generation unit 130.

In the second sequential stimulation treatment mode, the third magnetic field generation unit 130 operates for a predetermined time and stops, and after the third magnetic field generation unit 130 is stopped, the first magnetic field generation unit 110 operates for a predetermined time and stops, and after the first magnetic field generation unit 110 is stopped, the second magnetic field generation unit 120 operates for a predetermined time and stops, and after the second magnetic field generation unit 120 is stopped, the first magnetic field generation unit 110 operates for a predetermined time and stops, and after the first magnetic field generation unit 110 is stopped, the third magnetic field generation unit 130 operates for a predetermined time and stops.

That is, in the second sequential stimulation treatment mode, the operation is performed in the order of the third magnetic field generation unit 130, the first magnetic field generation unit 110, the second magnetic field generation unit 120, the first magnetic field generation unit 110, and the third magnetic field generation unit 130.

In addition, in the user mode, a patient or an operator such as a doctor may operate the apparatus by selecting the operation sequence and operation time of the first magnetic field generation unit 110, the second magnetic field generation unit 120, and the third magnetic field generation unit 130. In the user mode, the first magnetic field generation unit 110, the second magnetic field generation unit 120, and the third magnetic field generation unit 130 may be individually operated according to the operation sequence and operation time selected by a user, that is, a patient or an operator such as a doctor, so that individual treatment is possible depending on the patient's symptoms and severity of the symptoms.

FIGS. 2A to 2E are views showing stimulation patterns of the magnetic field generation units used in the apparatus for treating urinary incontinence using a magnetic field according to the present disclosure. FIG. 2A is a graph showing a stepwise stimulation pattern, FIG. 2B is a graph showing a trapezoidal stimulation pattern, FIG. 2C is a graph showing a first right triangle stimulation pattern in which frequency and intensity are gradually decreased over time, FIG. 2D is a graph showing a second right triangle stimulation pattern in which frequency and intensity are gradually increased over time, and FIG. 2E is a graph showing a waveform stimulation pattern.

To be specific, the stepwise stimulation pattern is a stimulation pattern in which frequency and intensity gradually increase in a stepwise manner and then gradually decrease in a stepwise manner over time.

The trapezoidal stimulation pattern is a stimulation pattern in which frequency and intensity gradually increase over time, are maintained constant for a certain period of time, and then gradually decrease.

The first right triangle stimulation pattern is a stimulation pattern in which the frequency and intensity have the highest values at the initial starting point, and gradually decrease as time passes to become zero (0).

The second right triangle stimulation pattern is a stimulation pattern in which frequency and intensity start at zero (0) at the initial starting point, and gradually increase as time passes to have predetermined maximum values at the preset final point.

The waveform stimulation pattern is a stimulation pattern in which frequency and intensity form a wave shape.

As described above, the stimulation pattern is divided into a frequency stimulation pattern and an intensity stimulation pattern. As the control unit 200, that is, the first magnetic field control unit 210, the second magnetic field control unit 220, and the third magnetic field control unit 230 divide the stimulation patterns of the magnetic fields generated by the first magnetic field generation unit 110, the second magnetic field generation unit 120, and the third magnetic field generation unit 130 controlled respectively by the first magnetic field control unit 210, the second magnetic field control unit 220, and the third magnetic field control unit 230 into frequency stimulation patterns and intensity stimulation patterns to generate complex stimulation patterns, thereby further enhancing treatment effects.

In other words, at least one of the first magnetic field generation unit 110, the second magnetic field generation unit 120, and the third magnetic field generation unit 130 may generate a magnetic field with a stimulation pattern different from the other two, with the stimulation pattern being divided into a frequency stimulation pattern and an intensity stimulation pattern. In addition, the first magnetic field generation unit 110, the second magnetic field generation unit 120, and the third magnetic field generation unit 130 may all generate magnetic fields with different stimulation patterns, with the stimulation patterns being divided into frequency stimulation patterns and intensity stimulation patterns.

As an example, the first magnetic field generation unit 110, the second magnetic field generation unit 120, and the third magnetic field generation unit 130 may generate frequency stimulation patterns in the same stimulation pattern, that is, the stepwise stimulation pattern, while generating intensity stimulation patterns in different stimulation patterns, that is, the trapezoidal stimulation pattern, first right triangle stimulation pattern, and waveform stimulation pattern, respectively.

Alternatively, the first magnetic field generation unit 110, the second magnetic field generation unit 120, and the third magnetic field generation unit 130 may generate frequency stimulation patterns in different stimulation patterns, that is, the stepwise stimulation pattern, trapezoidal stimulation pattern, and waveform stimulation pattern, respectively, while generating intensity stimulation patterns in the same stimulation pattern, that is, the second right triangle stimulation pattern.

The control unit 200 may control the operation of the first magnetic field generation unit 110, the second magnetic field generation unit 120, and the third magnetic field generation unit 130 such that each of the stepwise stimulation pattern, trapezoidal stimulation pattern, right triangle stimulation pattern, and waveform pattern is divided into a frequency stimulation pattern and an intensity stimulation pattern, and at least two of the stepwise stimulation pattern, the trapezoidal stimulation pattern, the right triangle stimulation pattern, and the waveform pattern are combined.

In the present disclosure, the first magnetic field generation unit 110, the second magnetic field generation unit 120, and the third magnetic field generation unit 130 generate magnetic fields in which at least two stimulation patterns of the stepwise stimulation pattern, trapezoidal stimulation pattern, right triangle stimulation pattern, and waveform pattern are combined, with the stimulation patterns being divided into frequency stimulation patterns and intensity stimulation patterns, thereby enhancing treatment effects.

Meanwhile, the control unit 200 controls the first magnetic field generation unit 110, the second magnetic field generation unit 120, and the third magnetic field generation unit 130 to generate magnetic fields having different frequency values, and these frequency values (e.g., 10 Hz or 50 HZ) are within the frequency range suitable for the corresponding muscle stimulated by the magnetic fields.

That is, the control unit 200 controls the strength of current supplied to each magnetic field probe so that a frequency value within the frequency range suitable for urinary incontinence treatment in the corresponding muscle stimulated by the first magnetic field generation unit 110, the second magnetic field generation unit 120, and the third magnetic field generation unit 130 may be generated from each magnetic field probe.

In addition, the control unit 200 controls the first magnetic field generation unit 110, the second magnetic field generation unit 120, and the third magnetic field generation unit 130 to generate magnetic fields having different frequency values, but to generate magnetic fields of different frequencies where interference waves are generated, so that effects of treating urinary incontinence may be improved.

The interference waves are known to relieve pain, balance nerves, and increase blood flow. Interference wave therapy is a treatment that utilizes advantages of medium frequency for greater depth of body penetration and of low frequency for effective tissue stimulation at the same time, and has effects such as pain relief, reduction of edema and inflammation, promotion of muscle contraction, and promotion of bone and soft tissue healing.

Figure 3:
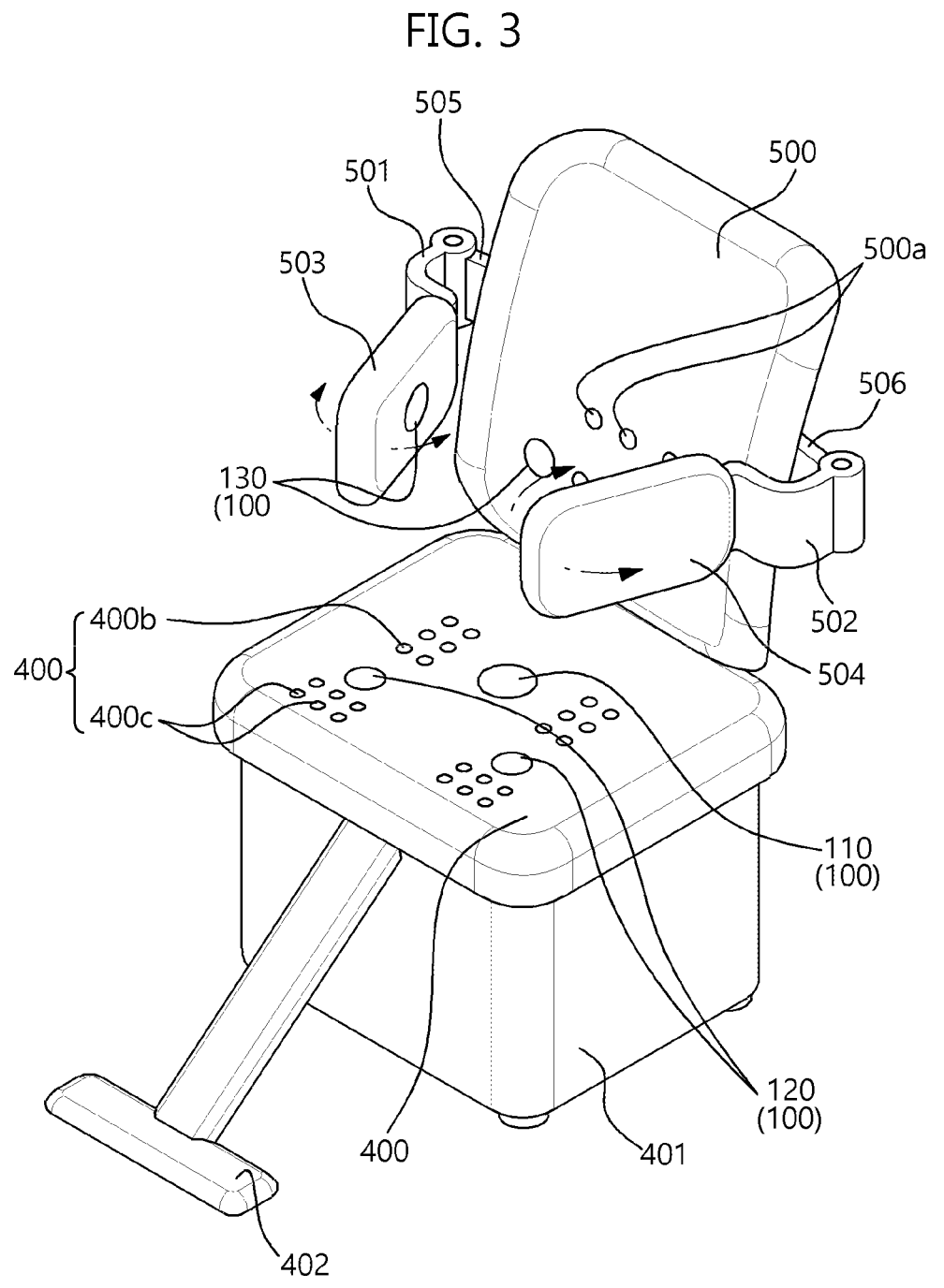

Meanwhile, FIG. 3 is a perspective view showing the embodiment of an apparatus for treating urinary incontinence using a magnetic field according to the present disclosure. Referring to FIG. 3, the embodiment of an apparatus for treating urinary incontinence using a magnetic field according to the present disclosure includes a seat portion 400 on which the first magnetic field generation unit 110 and the second magnetic field generation unit 120 are located and on which a patient may sit.

Since the pelvic floor muscles are located around the anus, the first magnetic field generation unit 110 is located in the center of the seat portion 400 on which the patient sits and generates a first magnetic field toward the pelvic floor muscles to electrically stimulate the pelvic floor muscles.

Since the adductor muscles are located in the thigh, the second magnetic field generation unit 120 is located at the part where the patient's thigh is positioned in the seat portion 400 where the patient sits, generates a second magnetic field to electrical stimulate the adductor muscles.

The second magnetic field generation unit 120 is mounted on the seat portion 400 in front of the first magnetic field generation unit 110 to be located at the parts where the patient's thighs are positioned when the patient sits on the seat portion 400.

The second magnetic field generation unit 120 may include a plurality of magnetic field probes spaced apart from each other in the longitudinal direction of the thigh to evenly apply the magnetic field to the entire thigh.

In addition, the embodiment of an apparatus for treating urinary incontinence using a magnetic field according to the present disclosure further includes a backrest portion 500 that is built on the rear side of the seat portion 400 to support the patient's back and where the third magnetic field generation unit 130 is located.

The backrest portion 500 is rotatably connected to the rear side of the seat portion 400 and is positioned so that an angle thereof may be adjusted.

In addition, the embodiment of an apparatus for treating urinary incontinence using a magnetic field according to the present disclosure may further include a seat support portion 401 located under the seat portion 400 to support the height of the seat portion 400.

The seat support portion 401 includes a seat lifting portion for moving the seat portion 400 up and down, so that the height of the seat portion 400 may be adjusted according to the height of the patient.

As an example, the seat lifting portion is a pneumatic cylinder capable of adjusting the height of the seat portion 400 according to the patient's height by moving the seat portion 400 up and down, and adjusting the height of the seat portion 400 with compressed air.

The angle adjustment structure of the backrest portion 500 and the lifting structure of the seat lifting portion may be variously modified from known chair structures, so detailed descriptions thereof will be omitted.

In addition, the embodiment of an apparatus for treating urinary incontinence using a magnetic field according to the present disclosure may further include a footrest portion 402 rotatably connected to the seat portion 400 or the seat support portion 401 and on which the patient's feet are placed.

The footrest portion 402 allows the patient's feet to be placed so that the patient may take a comfortable posture during the treatment procedure, and is rotatably connected to the seat portion 400 or the seat support portion 401 so that the position thereof may be adjusted according to the patient's posture or body shape.

Although not shown, an armrest capable of holding the patient's arms may be positioned on each side of the seat portion 400.

The backrest portion 500 has a first round part and a second round part at each side end thereof that are bent toward the patient's sides.

The third magnetic field generation unit 130 may effectively deliver a magnetic field to the transversus abdominis located on the lateral sides of the abdomen by positioning a magnetic field probe for generating a magnetic field on the side of the first round part and the side of the second round part.

In addition, since the transversus abdominis muscle is found in a location extending from the sides to the abdomen, the embodiment of an apparatus for treating urinary incontinence using a magnetic field according to the present disclosure further includes: a first arm member 501 and a second arm member 502 rotatably connected to each side of the backrest portion 500; a first transverse abdominis cover plate member 503 connected to the end of the first arm member 501, equipped with a third magnetic field generation unit 130, and positioned to cover the transversus abdominis muscle connected to the lateral side of the abdomen; and a second transverse abdominis cover plate member 504 connected to the end of the second arm member 502, equipped with a third magnetic field generation unit 130, and positioned to cover the transversus abdominis muscle connected to the lateral side of the abdomen.

The first transverse abdominis cover plate member 503 and the second transverse abdominis cover plate member 504 are located at the ends of the first arm member 501 and the second arm member 502, respectively, so as to cover the transversus abdominis muscle in the anterior part of the abdomen connected to the patient's sides by rotation of the first arm member 501 and the second arm member 502.

Magnetic field probes of the third magnetic field generation unit 130 are respectively positioned on the first transverse abdominis cover plate member 503 and the second transverse abdominis cover plate member 504 to generate magnetic fields applied to the transversus abdominis muscle in the anterior part of the abdomen connected to the patient's sides.

On the sides of the backrest portion 500, a first connection arm member 505 to which the first arm member 501 is rotatably connected, and a second connection arm member 506 to which the second arm member 502 is rotatably connected are respectively positioned.

The first transverse abdominis cover plate member 503 and the second transverse abdominis cover plate member 504 are positioned to cover the transversus abdominis muscle in the anterior part of the abdomen connected to the patient's sides by rotation of the first arm member 501 and the second arm member 502, so that the magnetic fields generated by the magnetic field probes are effectively transferred to the transversus abdominis muscle in the anterior part of the abdomen, increasing treatment effects.

In addition, the embodiment of an apparatus for treating urinary incontinence using a magnetic field according to the present disclosure may further include: a spacing adjustment moving unit 507 for adjusting the distance between the first transverse abdominis cover plate member 503 and the second transverse abdominis cover plate member 504 by moving the first transverse abdominis cover plate member 503 and the second transverse abdominis cover plate member 504 in the width direction of the backrest portion 500.

The spacing adjustment moving unit 507 includes a linear moving unit that linearly moves the first connection arm member 505 and the second connection arm member 506 to adjust the distance between the first transverse abdominis cover plate member 503 and the second transverse abdominis cover plate member 504.

For example, the linear moving unit may be a ball screw type linear actuator. The linear moving unit may be variously modified and implemented using known linear motion devices such as rack-and-pinion assemblies that convert rotational force of a motor into linear motion, including a rack gear and a pinion gear engaged with the rack gear and rotated by the motor, and thus a more detailed description is omitted.

Figure 4:
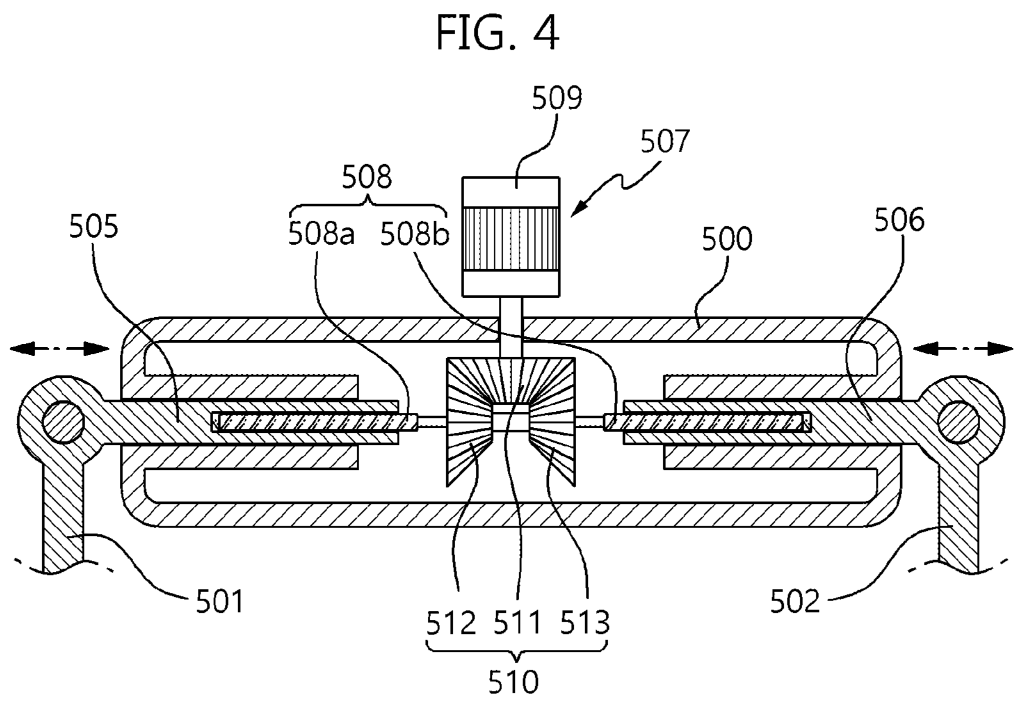
FIG. 4 is a view showing an example of a spacing adjustment moving unit in the embodiment of an apparatus for treating urinary incontinence using a magnetic field according to the present disclosure.

FIG. 4 is a view showing an example of a spacing adjustment moving unit in the embodiment of an apparatus for treating urinary incontinence using a magnetic field according to the present disclosure. Referring to FIG. 4, an example of a spacing adjustment moving unit may include: a moving screw unit 508 screwed one each into the first connection arm member 505 and the second connection arm member 506, but screwed in opposite directions to each other, to be rotatably positioned; and a rotary motor 509 that rotates the moving screw unit 508.

The moving screw unit 508 may include: a first screw 508*a* screwed to the first connection arm member 505 and rotatably positioned on the backrest portion 500; a second screw 508*b* that is screwed to the second connection arm member 506 and is screwed in the opposite direction to the screwing direction of the first screw 508*a* and is rotatably positioned on the backrest portion 500; and a power transmission unit for transmitting the rotational force of the rotary motor 509 to the first screw 508*a* and the second screw 508*b*.

The power transmission unit includes: a first bevel gear 511 coupled to a shaft of the rotary motor 509; a second bevel gear 512 positioned at one end of the first screw 508*a* and meshed with the first bevel gear 511; and a third bevel gear 513 positioned on the other end of the second screw 508*b* and meshed with the first bevel gear 511.

The first connection arm member 505 and the second connection arm member 506 are respectively screwed to the first screw and the second screw in opposite directions, respectively, and move towards or away from each other by rotation of the first screw and the second screw. As a result, the distance between the first transverse abdominis cover plate member 503 and the second transverse abdominis muscle cover plate member 504 may be narrowed or widened.

For example, the first connection arm member 505 is screwed to the first screw 508*a* in a left-handed direction while the second connection arm member 506 is screwed to the second screw 508*b* in a right-handed direction, but the screwing directions may be reversed.

The first transverse abdominis cover plate member 503 and the second transverse abdominis muscle cover plate member 504 may be positioned so as to cover the transverse abdominis muscle in the anterior part of the abdomen connected to the patient's sides while the distance between the first transverse abdominis cover plate member 503 and the second transverse abdominis muscle cover plate member 504 is adjusted by the operation of the spacing adjustment moving unit 507 according to the patient's body shape.

Figure 5:
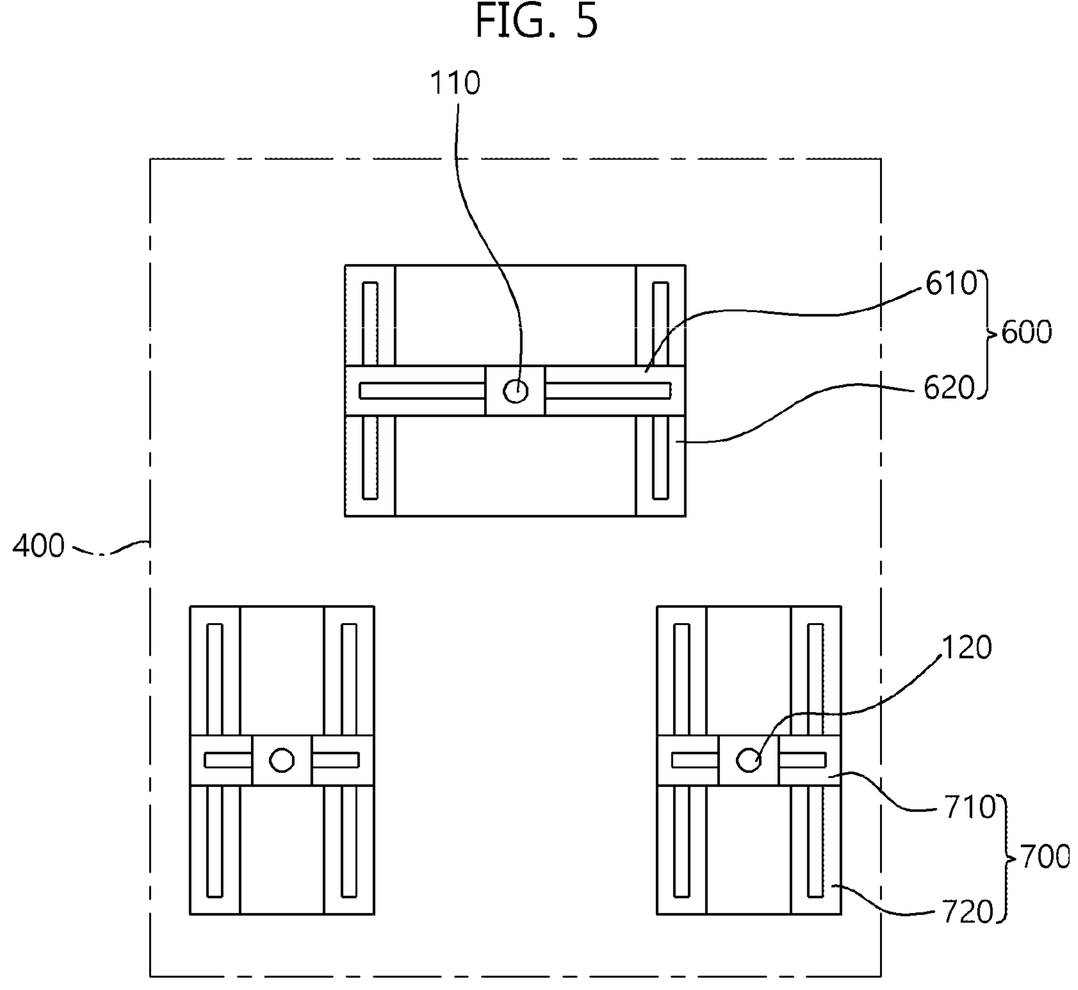
Figure 6:
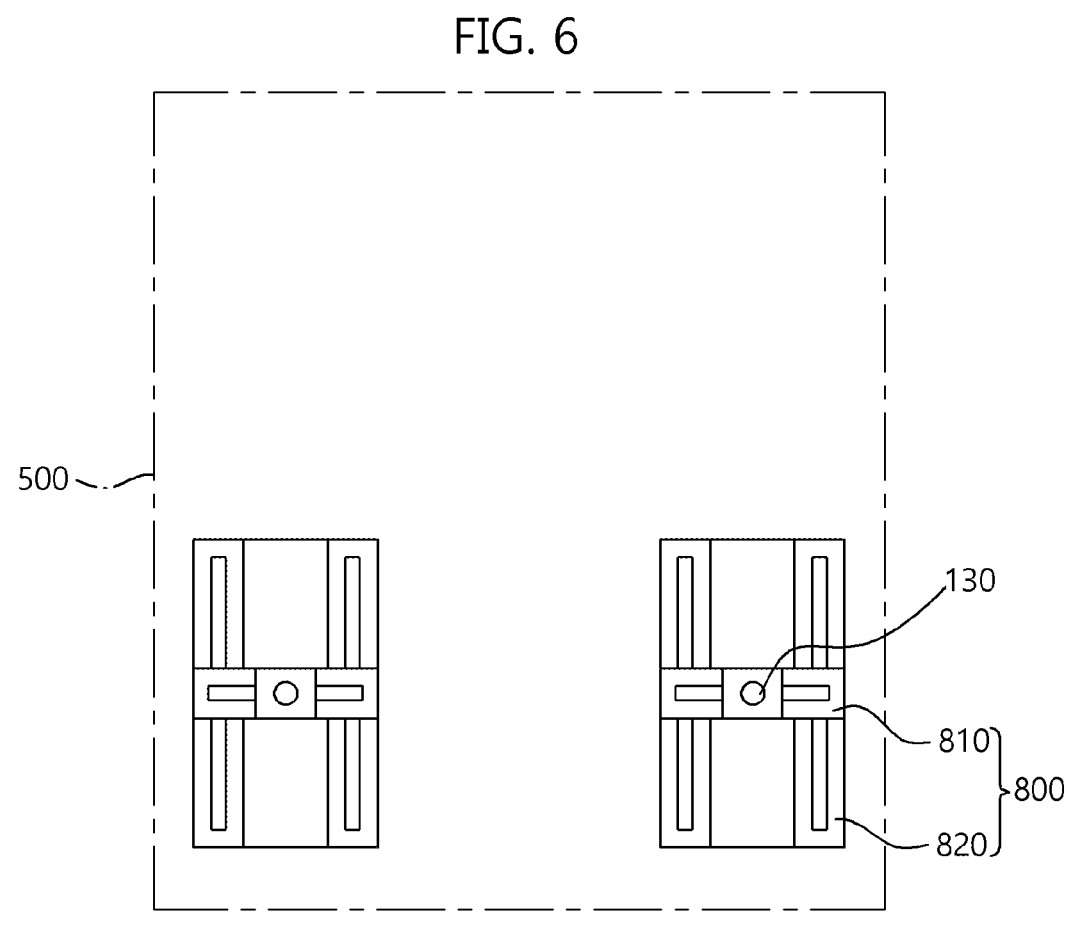

Meanwhile, FIGS. 5 and 6 are schematic views showing examples of a probe moving unit in the embodiment of an apparatus for treating urinary incontinence using a magnetic field according to the present disclosure. FIG. 5 shows a first probe moving unit 600 and a second probe moving unit 700 located on the seat portion 400, and FIG. 6 shows a third probe moving unit 800 located on the backrest portion 500.

Referring to FIGS. 5 and 6, the embodiment of an apparatus for treating urinary incontinence using a magnetic field according to the present disclosure may further include: the first probe moving unit 600 located on the seat portion 400 and moving the first magnetic field probe of the first magnetic field generation unit 110; and the second probe moving unit 700 for moving the second magnetic field probe of the second magnetic field generation unit 120.

The embodiment of an apparatus for treating urinary incontinence using a magnetic field according to the present disclosure may further include: the third probe moving unit 800 for moving the third magnetic field probe of the third magnetic field generation unit 130.

The first magnetic field generation unit 110 generates a magnetic field having a first frequency value through the first magnetic field probe, the second magnetic field generation unit 120 generates a magnetic field having a second frequency value through the second magnetic field probe; and the third magnetic field generation unit 130 generates a magnetic field having a third frequency value through the third magnetic field probe.

The first frequency value, the second frequency value, the third frequency value have different frequency values, and the first magnetic field probe, the second magnetic field probe, and the third magnetic field probe may generate interference waves through magnetic fields having different frequency values.

The first probe moving unit 600 moves the first magnetic field probe located at the center of the seat portion 400 and stimulating the pelvic floor muscles.

The second probe moving unit 700 is located on each side of the first probe moving unit 600 and moves the second magnetic field probe.

The third probe moving unit 800 is located on each side of the backrest and moves the third magnetic field probe.

To be specific, the first probe moving unit 600 may include: an X-axis linear moving portion for a first probe 610 on which the first magnetic field probe is mounted and which linearly reciprocates the mounted first magnetic field probe in the X-axis direction; and a Y-axis linear moving portion for a first probe 620 that linearly moves the X-axis linear moving portion for a first probe 610 in the Y-axis direction.

The X-axis linear moving portion for a first probe 610 and the Y-axis linear moving portion for a first probe 620 are, for example, a ball screw type linear actuators. The X-axis linear moving portion for a first probe 610 and the Y-axis linear moving portion for a first probe 620 may be variously modified and implemented using known linear motion devices such as rack-and-pinion assemblies that convert rotational force of a motor into linear motion, including a rack gear and a pinion gear engaged with the rack gear and rotated by the motor, and thus a more detailed description is omitted.

The first probe moving unit 600 may move the position of the first magnetic field probe to a desired position on a plane by moving the position of the first magnetic field probe in the X-axis direction and the Y-axis direction, respectively, by means of the X-axis linear moving portion for a first probe 610 and the Y-axis linear moving portion for a first probe 620.

In addition, the second probe moving unit 700 may include: an X-axis linear moving portion for a second probe 710 on which the second magnetic field probe is mounted and which linearly reciprocates the mounted second magnetic field probe in the X-axis direction; and a Y-axis linear moving portion for a second probe 720 that linearly moves the X-axis linear moving portion for a second probe 710 in the Y-axis direction.

The X-axis linear moving portion for a second probe 710 and the Y-axis linear moving portion for a second probe 720 are, for example, a ball screw type linear actuators. The X-axis linear moving portion for a second probe 710 and the Y-axis linear moving portion for a second probe 720 may be variously modified and implemented using known linear motion devices such as rack-and-pinion assemblies that convert rotational force of a motor into linear motion, including a rack gear and a pinion gear engaged with the rack gear and rotated by the motor, and thus a more detailed description is omitted.

The second probe moving unit 700 may move the position of the second magnetic field probe to a desired position on a plane by moving the position of the second magnetic field probe in the X-axis direction and the Y-axis direction, respectively, by means of the X-axis linear moving portion for a second probe 710 and the Y-axis linear moving portion for a second probe 720.

In addition, the third probe moving unit 800 may include: an X-axis linear moving portion for a third probe 810 on which the third magnetic field probe is mounted and which linearly reciprocates the mounted third magnetic field probe in the X-axis direction; and a Y-axis linear moving portion for a third probe 820 that linearly moves the X-axis linear moving portion for a third probe 810 in the Y-axis direction.

The X-axis linear moving portion for a third probe 810 and the Y-axis linear moving portion for a third probe 820 are, for example, a ball screw type linear actuators. The X-axis linear moving portion for a third probe 810 and the Y-axis linear moving portion for a third probe 820 may be variously modified and implemented using known linear motion devices such as rack-and-pinion assemblies that convert rotational force of a motor into linear motion, including a rack gear and a pinion gear engaged with the rack gear and rotated by the motor, and thus a more detailed description is omitted.

The third probe moving unit 800 may move the position of the third magnetic field probe to a desired position on a plane by moving the position of the third magnetic field probe in the X-axis direction and the Y-axis direction, respectively, by means of the X-axis linear moving portion for a third probe 810 and the Y-axis linear moving portion for a third probe 820.

Furthermore, the third probe moving unit 800 is located on the first transverse abdominis cover plate member 503 and the second transversus abdominis cover plate member 504, and moves the third magnetic field probe in the X-axis direction and the Y-axis direction, so that the magnetic field may be evenly delivered to the transverse abdominis muscle in the anterior part of the abdomen connected to the patient's sides.

During the treatment for urinary incontinence, the apparatus for treating urinary incontinence using a magnetic field according to the present disclosure may increase the effect of treating urinary incontinence by moving the magnetic field probes of the first magnetic field generation unit 110, the second magnetic field generation unit 120, and the third magnetic field generation unit 130 by means of the first probe moving unit 600, the second probe moving unit 700, and the third probe moving unit 800 and providing electrical stimulation through magnetic fields evenly to all parts of the major muscles affecting urinary incontinence.

In other words, during the treatment for urinary incontinence, the first magnetic field generation unit 110 and the second magnetic field generation unit 120 respectively may move the first magnetic field probe and the second magnetic field probe by means of the first probe moving unit 600 and the second probe moving unit 700 to apply magnetic fields evenly to the entire part of the pelvic floor muscles and the entire part of the adductor muscles, thereby increasing treatment effects.

In addition, during the treatment for urinary incontinence, the third magnetic field generation unit 130 may move the magnetic field probe by means of the third probe moving unit 800 to apply a magnetic field evenly to the entire part of the transversus abdominis muscle, thereby increasing treatment effects.

Meanwhile, referring back to FIG. 3, the embodiment of an apparatus for treating urinary incontinence using a magnetic field according to the present disclosure may further include: a plurality of seat pressure sensors 400*a* provided to be spaced apart on the seat portion 400 and detect pressure generated when the patient sits down; and a plurality of backrest pressure sensors 500*a* provided to be spaced apart on the backrest portion 500 and detect pressure generated when the patient leans against the backrest portion 500.

The control unit 200 receives pressure values from the seat pressure sensors 400*a* and the backrest pressure sensors 500*a* and checks the body shape and posture of the seated patient. Then, according to the body shape and posture of the patient, the control unit 200 positions the magnetic field probes, that is, the first magnetic field probe, the second magnetic field probe, and the third magnetic field probe to face the corresponding muscles for treatment of urinary incontinence, that is, the pelvic floor muscles, adductor muscles, and transversus abdominis muscle, respectively, by means of the first probe moving unit 600, the second probe moving unit 700, and the third probe moving unit 800.

To be specific, the seat pressure sensors 400*a* include: a plurality of first pressure sensor portions 400*b* located in parts of the seat portion 400 where the patient's buttocks are positioned; and a plurality of second pressure sensor portions 400*c* located in parts of the seat portion 400 where the patient's thighs are positioned.

In addition, the control unit 200 stores pressure values that are differently detected by the seat pressure sensors 400*a* and the backrest pressure sensors 500*a* depending on the patient's body shape and posture when the patient sits on the seat portion 400, and includes a data storage unit for storing position information of each of the plurality of magnetic field probes based on the patient's body shape and posture.

The control unit 200 compares the pressure values detected by the first pressure sensor portions 400*b* and the second pressure sensor portions 400*c* when the patient sits on the seat portion 400 and leans his/her back against the backrest portion 500 with data previously stored in the data storage unit to determine the patient's body shape and posture.

After determining the patient's body shape and posture, the control unit 200 positions the magnetic field probes, that is, the first magnetic field probe, the second magnetic field probe, and the third magnetic field probe to face the pelvic floor muscles, adductor muscles, and transversus abdominis muscle, respectively, according to the body shape and posture of the patient by means of the first probe moving unit 600, the second probe moving unit 700, and the third probe moving unit 800, and then moves the magnetic field probes so that the magnetic fields are evenly applied to all parts of the pelvic floor muscles, adductor muscles, and transversus abdominis muscle, thereby greatly improving treatment effects.

Figure 7:
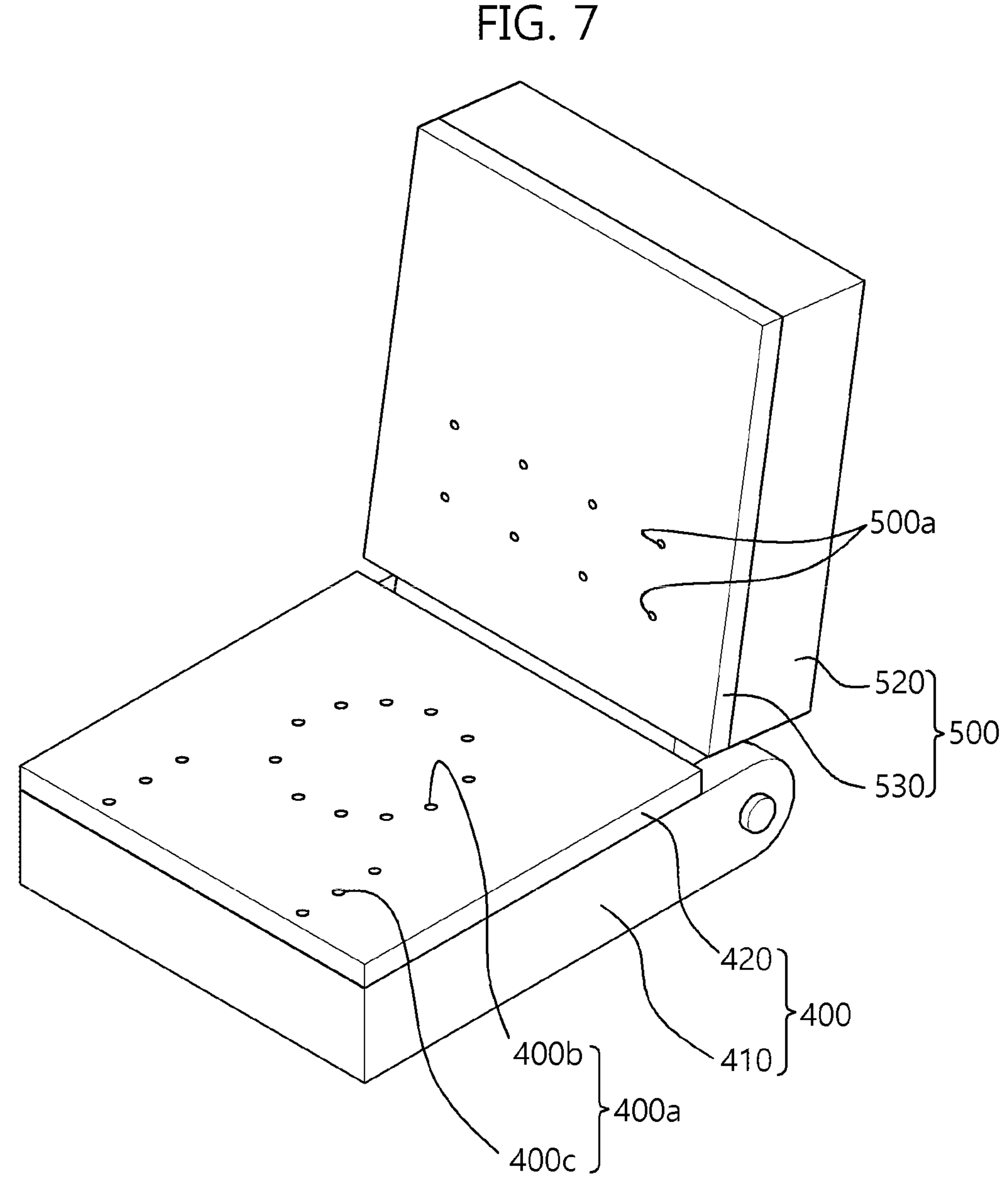
FIG. 7 is a perspective view showing another embodiment of an apparatus for treating urinary incontinence using a magnetic field according to the present disclosure.
Figure 8:
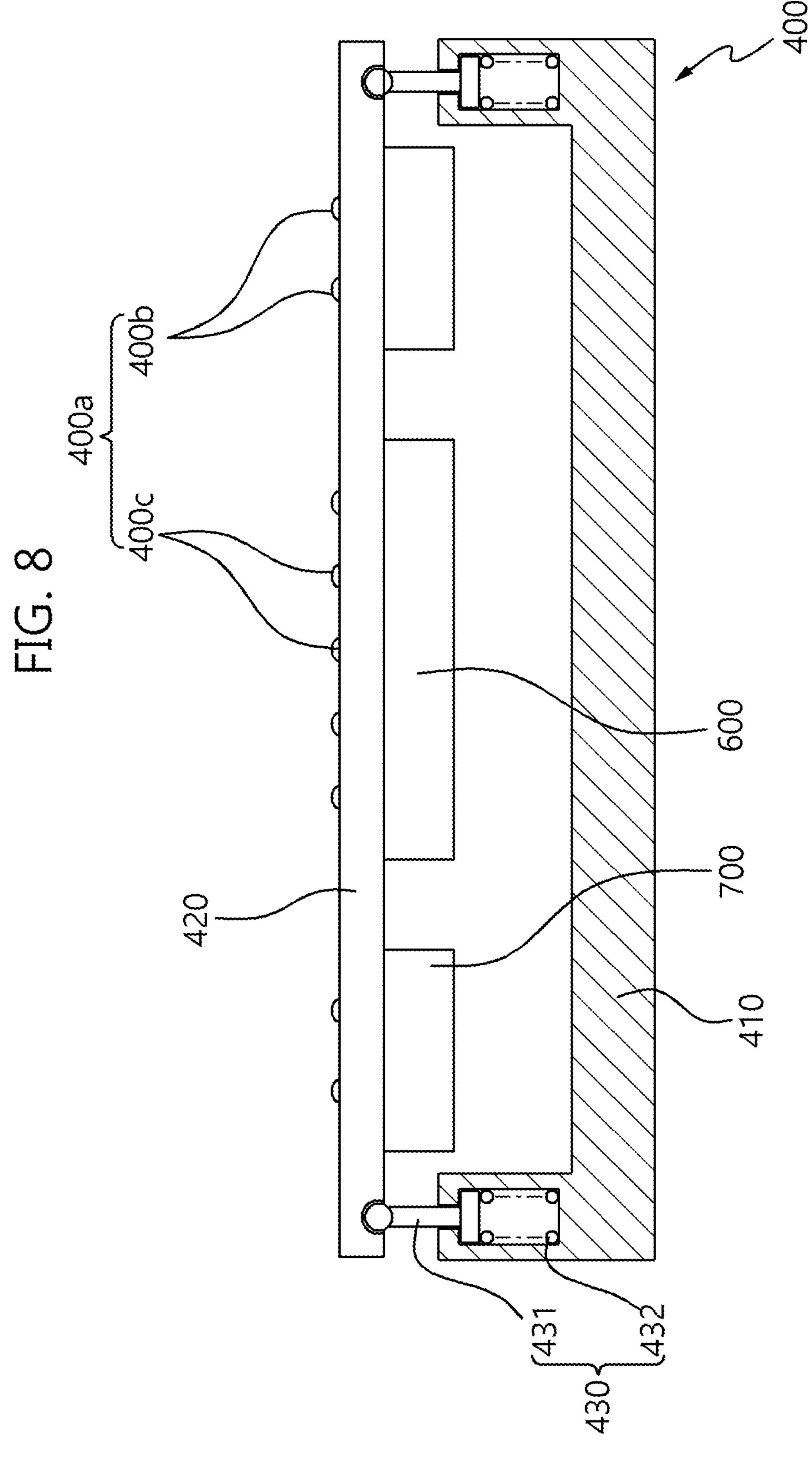
FIG. 8 is a cross-sectional view showing a seat portion in another embodiment of an apparatus for treating urinary incontinence using a magnetic field according to the present disclosure.
Figure 9:
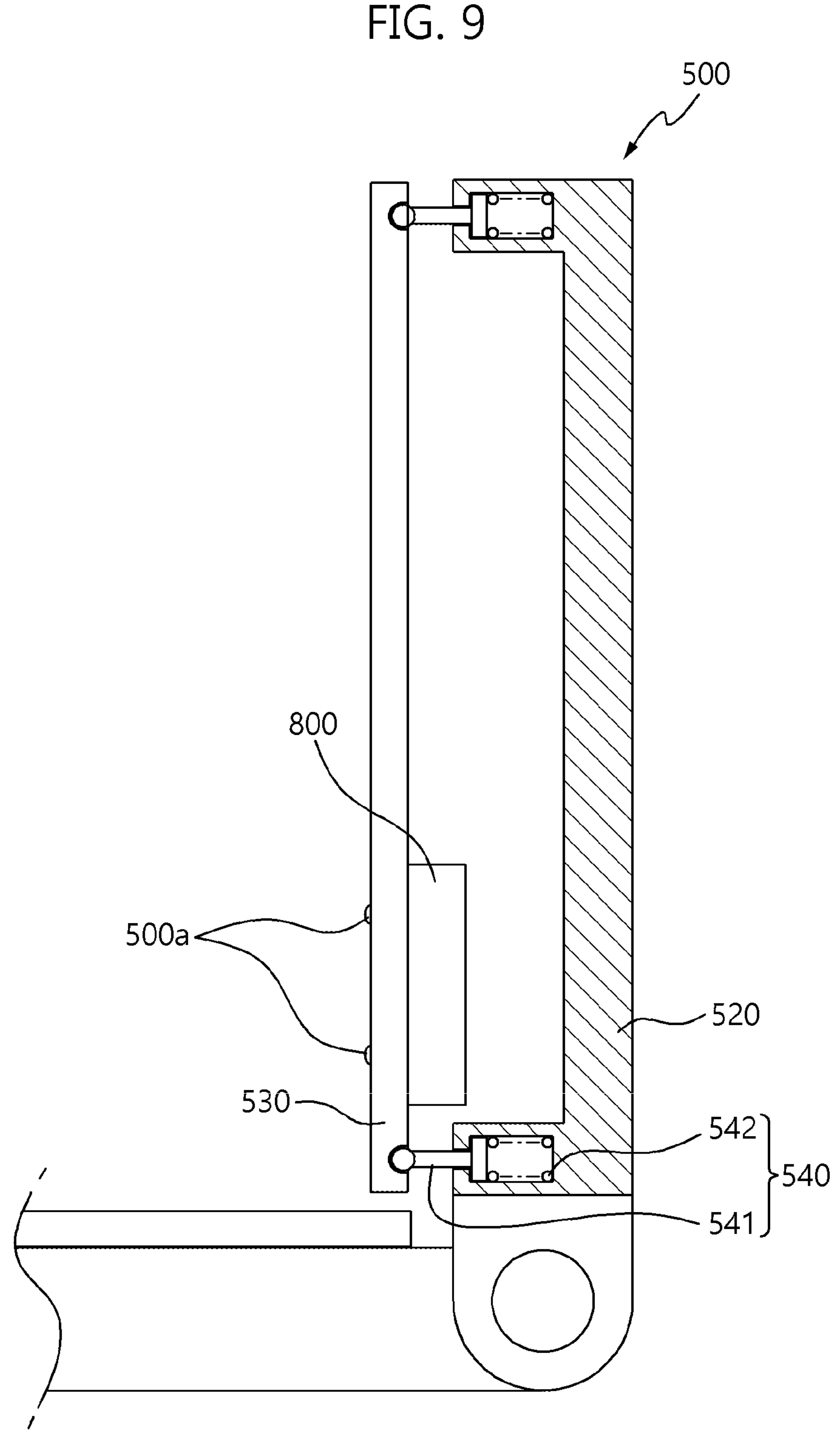
FIG. 9 is a cross-sectional view showing a backrest portion in another embodiment of an apparatus for treating urinary incontinence using a magnetic field according to the present disclosure.

Meanwhile, FIG. 7 is a perspective view showing another embodiment of an apparatus for treating urinary incontinence using a magnetic field according to the present disclosure, FIG. 8 is a cross-sectional view showing a seat portion 400 in another embodiment of an apparatus for treating urinary incontinence using a magnetic field according to the present disclosure, and FIG. 9 is a cross-sectional view showing a backrest portion 500 in another embodiment of an apparatus for treating urinary incontinence using a magnetic field according to the present disclosure.

Another embodiment of an apparatus for treating urinary incontinence using a magnetic field according to the present disclosure is described in detail below.

The seat portion 400 includes a seat casing portion 410 and 420 where a first magnetic field generation unit 110 and a second magnetic field generation unit 120 are located, and the backrest portion 500 includes a backrest casing portion 510 and 520 where a third magnetic field generation unit 130 is located.

Although not shown, the seat portion 400 may further include a seat cover surrounding the seat casing portion 410 and 420, and made of natural or synthetic resin material.

Although not shown, the backrest portion 500 may further include a backrest cover surrounding the backrest casing portion 510 and 520, and made of natural or synthetic resin material.

The unillustrated seat cover and the backrest cover may be variously modified and implemented in a known cover structure that wraps the seat and backrest in a known chair, and thus detailed descriptions thereof are omitted.

The seat casing portion 410 and 420 may include: a seat body casing member 410 having an open upper surface; a seat casing cover member 420 that covers the open upper surface of the seat body casing member 410; and a seat cover elastic support 430 that elastically supports the seat casing cover member 420.

The seat cover elastic support 430 includes: a plurality of seat cover moving members 431 protruding toward the lower side of the seat casing cover member 420 and movably inserted into the side surface of the seat body casing member 410; and a seat cover spring member 432 located in the side portion of the seat body casing member 410 and elastically supporting the seat cover moving members 431.

A ball joint rotatably coupled to the seat casing cover member 420 is located at the upper end of the seat cover moving members 431, so that the seat casing cover member 420 may be elastically supported by the seat cover spring member 432 while being freely inclined and positioned according to the patient's sitting posture.

Since the seat casing cover member 420 is elastically supported by the seat cover elastic support 430, the seat casing portion may provide the patient with a feeling of softness and comfort while sitting, which minimizes discomfort during treatment.

The backrest casing portion may include: a backrest body casing member 520 having an open upper surface and in which the third probe moving unit 800 is located therein; a backrest casing cover member 530 that covers the open upper surface of the backrest body casing member 520; and a backrest cover elastic support 540 that elastically supports the backrest casing cover member 530.

The backrest cover elastic support 540 includes: a plurality of backrest cover moving members 541 protruding toward the rear side of the backrest casing cover member 530 and movably inserted into the side surface of the backrest body casing member 520; and a backrest cover spring member 542 located in the side surface of the backrest body casing member 520 and elastically supporting the backrest cover moving members 541.

A ball joint rotatably coupled to the backrest casing cover member 530 is located at one end of the backrest cover moving members 541, so that the backrest casing cover member 530 may be elastically supported by the backrest cover spring member 542 while being freely inclined and positioned according to the patient's sitting posture.

Since the backrest casing cover member 530 is elastically supported by the backrest cover elastic support 540, the backrest casing portion provide the patient with a feeling of softness and comfort while sitting and leaning, which minimizes discomfort during treatment.

The present disclosure may improve effect of treating urinary incontinence by simultaneously stimulating major muscles involved in urinary incontinence using a plurality of magnetic field probes.

The present disclosure may further improve effect of treating urinary incontinence by mixing frequencies generated and forms of stimulation applied by a plurality of magnetic field probes or by using interference waves generated by the probes that generate different frequencies.

The present disclosure can further improve effect of treating urinary incontinence by adjusting the position of each magnetic field probe that applies magnetic field stimulation to muscles according to the patient's muscle condition or posture.

It is to be noted that the present disclosure is not limited to the above embodiments, and may be implemented with various changes without departing from the gist of the present disclosure, which is included in the configuration of the present disclosure.

The invention claimed is:

1. An apparatus for treating urinary incontinence using a magnetic field, the apparatus comprising:

magnetic field generation units configured to apply magnetic fields to different muscles of a patient, the muscles being muscles that affect a treatment of the urinary incontinence of the patient;

a control unit configured to control an operation of the magnetic field generation units;

a power supply unit configured to supply power to the magnetic field generation units and the control unit, wherein the magnetic field generation units comprise:

a first magnetic field generation unit configured to apply a magnetic field to pelvic floor muscles of the patient; and a second magnetic field generation unit configured to apply a magnetic field to adductor muscles of the patient, a seat portion on which the first magnetic field generation unit and the second magnetic field generation unit are located and on which the patient sits;

a first probe moving unit located on the seat portion and configured to move a first magnetic field probe of the first magnetic field generation unit;

a second probe moving unit configured to move a second magnetic field probe of the second magnetic field generation unit, wherein the first probe moving unit comprises:

an X-axis linear moving portion for a first probe on which the first magnetic field probe is mounted, and configured to linearly reciprocate the mounted first magnetic field probe in an X-axis direction; and a Y-axis linear moving portion for the first probe configured to linearly move the X-axis linear moving portion for the first probe in a Y-axis direction, and the second probe moving unit comprises:

an X-axis linear moving portion for a second probe on which the second magnetic field probe is mounted, and configured to linearly reciprocate the mounted second magnetic field probe in the X-axis direction; and a Y-axis linear moving portion for the second probe configured to linearly move the X-axis linear moving portion for the second probe in the Y-axis direction.

2. The apparatus of claim 1, wherein the magnetic field generation units further comprise:

a third magnetic field generation unit configured to apply a magnetic field to transversus abdominis muscles of the patient.

3. The apparatus of claim 2, wherein the control unit comprises a treatment mode unit for treating urinary incontinence according to a predetermined stimulation area and stimulation sequence, and a user mode unit with which the patient or an operator is able to select a stimulation area and stimulation sequence, wherein the treatment mode unit comprises the predetermined stimulation area, and treatment modes for stimulating the predetermined stimulation area according to a predetermined sequence, wherein the treatment modes comprise:

a circulation operation mode in which the first magnetic field generation unit, the second magnetic field generation unit, and the third magnetic field generation unit are operated cyclically in random order but operated individually;

a complex stimulation cycle mode in which at least two of the first magnetic field generation unit, the second magnetic field generation unit, and the third magnetic field generation unit are operated at the same time to apply complex stimulation, but different complex stimulations are applied cyclically; and a sequential stimulation treatment mode in which the first magnetic field generation unit, the second magnetic field generation unit, and the third magnetic field generation unit are operated sequentially in random order.

4. The apparatus of claim 2, wherein the control unit controls operations of the first magnetic field generation unit, the second magnetic field generation unit, and the third magnetic field generation unit to generate magnetic fields having at least two different stimulation patterns.

5. The apparatus of claim 2, further comprising:

a backrest portion that is built on a rear side of the seat portion to support the patient's back and on which the third magnetic field generation unit is located.

6. The apparatus of claim 5, further comprising:

a first arm member and a second arm member rotatably connected to each side of the backrest portion;

a first transverse abdominis cover plate member connected to an end of the first arm member, equipped with the third magnetic field generation unit, and positioned to cover the transversus abdominis muscles connected to a side of an abdomen; and a second transverse abdominis cover plate member connected to an end of the second arm member, equipped with the third magnetic field generation unit, and positioned to cover the transversus abdominis muscles connected to a side of the abdomen.

7. The apparatus of claim 6, further comprising:

a spacing adjustment moving unit configured to adjust a distance between the first transverse abdominis cover plate member and the second transverse abdominis cover plate member by moving the first transverse abdominis cover plate member and the second transverse abdominis cover plate member in a width direction of the backrest portion.

8. The apparatus of claim 7, wherein on each side of the backrest portion, a first connection arm member to which the first arm member is rotatably connected, and a second connection arm member to which the second arm member is rotatably connected are respectively positioned, and wherein the spacing adjustment moving unit comprises:

a plurality of moving screw units screwed into the first connection arm member and the second connection arm member, but in opposite directions to each other, to be rotatably positioned; and a rotary motor configured to rotate the moving screw units.

9. The apparatus of claim 5, further comprising:

a third probe moving unit configured to move a third magnetic field probe of the third magnetic field generation unit.

10. The apparatus of claim 9, wherein the third probe moving unit comprises:

an X-axis linear moving portion for a third probe on which the third magnetic field probe is mounted, and configured to linearly reciprocate the mounted third magnetic field probe in the X-axis direction; and a Y-axis linear moving portion for a third probe configured to linearly move the X-axis linear moving portion for a third probe in the Y-axis direction.

11. The apparatus of claim 9, further comprising:

seat pressure sensors provided to be spaced apart on the seat portion and detect pressure generated when the patient sits down; and backrest pressure sensors provided to be spaced apart on the backrest portion and detect pressure generated when the patient leans against the backrest portion, wherein the control unit receives pressure values from the seat pressure sensors and the backrest pressure sensors, checks a body shape and a posture of the seated patient, and, according to the body shape and the posture of the patient, positions the first magnetic field probe, the second magnetic field probe, and the third magnetic field probe to face the pelvic floor muscles, the adductor muscles, and the transversus abdominis muscles, respectively, for the treatment of the urinary incontinence by means of the first probe moving unit, the second probe moving unit, and the third probe moving unit.

12. The apparatus of claim 5, wherein the backrest portion comprises a backrest casing portion where the third magnetic field generation unit is located, wherein the backrest casing portion comprises:

a backrest body casing member having an open upper surface;

a backrest casing cover member configured to cover the open upper surface of the backrest body casing member; and a backrest cover elastic support configured to elastically support the backrest casing cover member, wherein the backrest cover elastic support comprises:

backrest cover moving members protruding toward a rear side of the backrest casing cover member and movably inserted into a side surface of the backrest body casing member; and a backrest cover spring member located in the side surface of the backrest body casing member and elastically supporting the backrest cover moving members, wherein at one end of the backrest cover moving members, a ball joint rotatably coupled to the backrest casing cover member is located.

13. The apparatus of claim 1, further comprising:

seat pressure sensors provided to be spaced apart on the seat portion and detect pressure generated when the patient sits down, wherein the control unit receives pressure values from the seat pressure sensors, checks a body shape and a posture of the seated patient, and, according to the body shape and the posture of the patient, positions the first magnetic field probe and the second magnetic field probe to face the pelvic floor muscles and the adductor muscles, respectively, for the treatment of the urinary incontinence by means of the first probe moving unit and the second probe moving unit.

14. An apparatus for treating urinary incontinence using a magnetic field, the apparatus comprising:

magnetic field generation units configured to apply magnetic fields to different muscles of a patient, the muscles being muscles that affect a treatment of the urinary incontinence of the patient;

a control unit configured to control an operation of the magnetic field generation units;

a power supply unit configured to supply power to the magnetic field generation units and the control unit;

wherein the magnetic field generation units comprise:

a first magnetic field generation unit configured to apply a magnetic field to pelvic floor muscles of the patient; and a second magnetic field generation unit configured to apply a magnetic field to adductor muscles of the patient, a seat portion on which the first magnetic field generation unit and the second magnetic field generation unit are located and on which the patient sits, wherein the seat portion comprises a seat casing portion where the first magnetic field generation unit and the second magnetic field generation unit are located, wherein the seat casing portion comprises:

a seat body casing member having an open upper surface;

a seat casing cover member configured to cover the open upper surface of the seat body casing member; and a seat cover elastic support configured to elastically support the seat casing cover member, wherein the seat cover elastic support comprises:

seat cover moving members protruding toward a lower side of the seat casing cover member and movably inserted into a side surface of the seat body casing member; and a seat cover spring member located in a side portion of the seat body casing member and elastically supporting the seat cover moving members, wherein at an upper end of the seat cover moving members, a ball joint rotatably coupled to the seat casing cover member is located.

* * * * *